(12) United States Patent
Fairhurst et al.

(10) Patent No.: US 9,296,733 B2
(45) Date of Patent: Mar. 29, 2016

(54) OXAZOLIDIN-2-ONE-PYRIMIDINE DERIVATIVE AND USE THEREOF FOR THE TREATMENT OF CONDITIONS, DISEASES AND DISORDERS DEPENDENT UPON PI3 KINASES

(71) Applicants: Robin Alec Fairhurst, Riehen (CH); Pascal Furet, Thann (FR); Frank Stephan Kalthoff, Guntramsdorf (AT); Andreas Lerchner, Binningen (CH); Heinrich Rueeger, Flueh (CH)

(72) Inventors: Robin Alec Fairhurst, Riehen (CH); Pascal Furet, Thann (FR); Frank Stephan Kalthoff, Guntramsdorf (AT); Andreas Lerchner, Binningen (CH); Heinrich Rueeger, Flueh (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/069,400

(22) Filed: Nov. 1, 2013

(65) Prior Publication Data

US 2014/0135330 A1      May 15, 2014

Related U.S. Application Data

(60) Provisional application No. 61/725,113, filed on Nov. 12, 2012.

(51) Int. Cl.
| | |
|---|---|
| *A61K 31/5377* | (2006.01) |
| *C07D 413/14* | (2006.01) |
| *A61K 45/06* | (2006.01) |
| *C07D 417/14* | (2006.01) |

(52) U.S. Cl.
CPC .......... *C07D 413/14* (2013.01); *A61K 31/5377* (2013.01); *A61K 45/06* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 3,975,384 A | 8/1976 | Narr et al. | |
| 4,929,726 A | 5/1990 | Strekowski et al. | |
| 5,358,945 A | 10/1994 | Mizuchi et al. | |
| 5,786,355 A | 7/1998 | Konno et al. | |
| 5,976,758 A | 11/1999 | Fukui et al. | |
| 5,990,105 A | 11/1999 | Bos et al. | |
| 6,251,900 B1 | 6/2001 | Kawashima et al. | |
| 6,288,228 B1 | 9/2001 | Henkin et al. | |
| 6,495,558 B1 | 12/2002 | Armistead et al. | |
| 6,599,926 B2 | 7/2003 | Pinto et al. | |
| 6,603,000 B2 | 8/2003 | Yee et al. | |
| 6,743,788 B2 | 6/2004 | Cirillo et al. | |
| 6,846,928 B2 | 1/2005 | Wang et al. | |
| 7,045,519 B2 | 5/2006 | Nuss et al. | |
| 7,091,343 B2 | 8/2006 | Bebbington et al. | |
| 7,179,826 B2 | 2/2007 | Bebbington et al. | |
| 7,423,148 B2 | 9/2008 | Nuss et al. | |
| 7,566,712 B2 | 7/2009 | Bakthavatchalam et al. | |
| 7,652,009 B2 * | 1/2010 | Kim et al. | 514/252.04 |
| 7,767,669 B2 | 8/2010 | Nuss et al. | |
| 7,893,063 B2 | 2/2011 | Pass | |
| 7,957,951 B2 | 6/2011 | Foster et al. | |
| 8,173,647 B2 | 5/2012 | Atallah et al. | |
| 8,217,035 B2 | 7/2012 | Burger et al. | |
| 8,563,549 B2 | 10/2013 | Burger et al. | |
| 8,575,338 B2 | 11/2013 | Tsuzuki et al. | |
| 8,865,894 B2 | 10/2014 | Caravatti et al. | |
| 2004/0002496 A1 | 1/2004 | Bebbington et al. | |
| 2004/0009974 A1 | 1/2004 | Bebbington et al. | |
| 2004/0009981 A1 | 1/2004 | Bebbington et al. | |
| 2005/0014753 A1 | 1/2005 | Ding et al. | |
| 2009/0018134 A1 | 1/2009 | Pike et al. | |
| 2010/0048547 A1 | 2/2010 | Atallah et al. | |
| 2010/0249126 A1 | 9/2010 | Burger et al. | |
| 2011/0195966 A1 | 8/2011 | Garcia-Echeverria et al. | |
| 2012/0225859 A1 | 9/2012 | Burger et al. | |
| 2013/0123289 A1 | 5/2013 | Yang et al. | |
| 2013/0143862 A1 | 6/2013 | Ashcraft et al. | |
| 2013/0150368 A1 | 6/2013 | Ashcraft et al. | |
| 2013/0225574 A1 | 8/2013 | Caravatti et al. | |
| 2014/0135330 A1 | 5/2014 | Fairhurst et al. | |
| 2014/0235620 A1 | 8/2014 | Cho et al. | |
| 2014/0275083 A1 | 9/2014 | Caferro et al. | |

FOREIGN PATENT DOCUMENTS

| | | |
|---|---|---|
| AU | 2010291318 A2 | 3/2011 |
| CN | 103483345 | 1/2014 |
| CN | 103694218 | 4/2014 |
| DE | 2341925 A1 | 3/1975 |
| EP | 0330263 A1 | 8/1989 |
| EP | 0459830 A1 | 12/1991 |
| EP | 0767170 B1 | 10/2002 |
| EP | 1277738 A1 | 1/2003 |
| EP | 1277741 A1 | 1/2003 |
| EP | 2 394 999 | 12/2011 |

(Continued)

OTHER PUBLICATIONS

Burger et al, "Identification of NVP-BKM120 as a Potent, Selective, Orally Bioavailable Class I PI3 Kinase Inhibitor for Treating Cancer," ACS Med. Chem. Lett. 2(10), 774-779 (2011).

(Continued)

*Primary Examiner* — Alicia L Otton
*Assistant Examiner* — Jeanmarie Calvillo
(74) *Attorney, Agent, or Firm* — John B. Alexander

(57) ABSTRACT

The present invention relates to oxazolidin-2-one substituted pyrimidine compounds that act as PI3K (phosphatidylinositol-3-kinase) inhibitors, as well as pharmaceutical compositions thereof, methods for their manufacture and uses for the treatment of conditions, diseases and disorders dependent on PI3K.

5 Claims, No Drawings

(56) References Cited

FOREIGN PATENT DOCUMENTS

| | | |
|---|---|---|
| EP | 2 560 488 | 2/2013 |
| EP | 2 563 365 | 3/2013 |
| GB | 581334 A | 10/1946 |
| GB | 2431156 A | 4/2007 |
| JP | 49021148 B | 2/1974 |
| JP | 49021149 B | 2/1974 |
| JP | 11158073 A2 | 6/1999 |
| JP | 2001089452 A | 4/2001 |
| WO | 8900599 A1 | 1/1989 |
| WO | 9919305 A2 | 4/1999 |
| WO | 9965897 A1 | 12/1999 |
| WO | 0043373 A2 | 7/2000 |
| WO | 0100207 A1 | 1/2001 |
| WO | 0100213 A1 | 1/2001 |
| WO | 0100214 A1 | 1/2001 |
| WO | 0105783 A1 | 1/2001 |
| WO | 01/60816 | 8/2001 |
| WO | 0172745 A1 | 10/2001 |
| WO | 0183456 A1 | 11/2001 |
| WO | 0220495 A2 | 3/2002 |
| WO | 0222606 A1 | 3/2002 |
| WO | 0222608 A1 | 3/2002 |
| WO | 0236586 A1 | 5/2002 |
| WO | 02062766 A2 | 8/2002 |
| WO | 02062789 A1 | 8/2002 |
| WO | 02064096 A2 | 8/2002 |
| WO | 02102313 A2 | 12/2002 |
| WO | 03030909 A1 | 4/2003 |
| WO | 2004000820 A2 | 12/2003 |
| WO | 2004029204 A2 | 4/2004 |
| WO | 2004032716 A2 | 4/2004 |
| WO | 2004/039788 | 5/2004 |
| WO | 2004048365 A1 | 6/2004 |
| WO | 2004084824 A2 | 10/2004 |
| WO | 2004092196 A2 | 10/2004 |
| WO | 2005007648 A2 | 1/2005 |
| WO | 2005009977 A1 | 2/2005 |
| WO | 2005028444 A1 | 3/2005 |
| WO | 2005099711 A1 | 10/2005 |
| WO | 2006005914 A1 | 1/2006 |
| WO | 2006026135 A2 | 3/2006 |
| WO | 2006065872 A1 | 6/2006 |
| WO | 2006071538 A2 | 7/2006 |
| WO | 2006071960 A2 | 7/2006 |
| WO | 2006078992 A2 | 7/2006 |
| WO | 2006090167 A2 | 8/2006 |
| WO | 2006113704 A2 | 10/2006 |
| WO | 2007080382 A1 | 7/2007 |
| WO | 2007084786 A1 | 7/2007 |
| WO | 2008/080937 | 7/2008 |
| WO | 2008098058 A1 | 8/2008 |
| WO | 2009007748 A2 | 1/2009 |
| WO | 2009066084 A1 | 5/2009 |
| WO | 2009109605 A1 | 9/2009 |
| WO | 2009118324 A1 | 10/2009 |
| WO | 2009120094 A2 | 10/2009 |
| WO | 2009125870 A1 | 10/2009 |
| WO | 2010/020432 | 2/2010 |
| WO | 2010/049481 | 5/2010 |
| WO | 2010052569 A2 | 5/2010 |
| WO | 2010068863 A2 | 6/2010 |
| WO | 2010/090290 | 8/2010 |
| WO | 2010/090344 | 8/2010 |
| WO | 2010/105243 | 9/2010 |
| WO | 2010120994 A2 | 10/2010 |
| WO | 2010/135070 | 11/2010 |
| WO | 2011005119 A1 | 1/2011 |
| WO | 2011017296 A1 | 2/2011 |
| WO | 2011026835 A1 | 3/2011 |
| WO | 2011031896 A2 | 3/2011 |
| WO | 2011/072174 | 6/2011 |
| WO | 2011114275 A1 | 9/2011 |
| WO | 2011/133888 | 10/2011 |
| WO | 2011/143160 | 11/2011 |
| WO | 2012/009678 | 1/2012 |
| WO | 2012044727 A2 | 4/2012 |
| WO | 2012054535 A2 | 4/2012 |
| WO | 2012055942 A1 | 5/2012 |
| WO | 2012109423 A1 | 8/2012 |
| WO | 2012/171337 | 12/2012 |
| WO | 2013/030368 | 3/2013 |
| WO | 2013/046136 | 4/2013 |
| WO | 2013/052395 | 4/2013 |
| WO | 2013/124826 | 8/2013 |
| WO | WO 2013/173283 A1 * 11/2013 ......... A61K 31/5377 |
| WO | 2013/184621 | 12/2013 |
| WO | 2014/028566 | 2/2014 |
| WO | 2014/064058 | 5/2014 |
| WO | 2014/141104 | 9/2014 |
| WO | 2014/141153 | 9/2014 |

OTHER PUBLICATIONS

Patani, et al., "Bioisosterism: A Rational Approach in Drug Design", Chem. Rev. 96(8):3147-3176 (1996).
Silverman, et al., "The Organic Chemistry of Drug Design and Drug Action," Elsevier Acadamic Press 2nd ed., 29-34 (2004).
Katiyar, et al., "Syntheses of 2,4,6-Trisubstituted Pyrimidine Derivatives as a New Class of Antifilarial Topoisomerase II Inhibitors," Bioorganic & Medicinal Chemistry Letters 15:47-50 (2005).
Mokrosz.et al., "4-(3-Furyl)-2-(4-Methylpiperazino)Pyrimidines: Potent 5-HT2A Receptor Antagonists", Bioorganic & Medicinal Chemistry Letters 7(13):1635-1638 (1997).
Sukhwal et al., "A New Route to 2-Piperidino-4, 6-diarylpyrimidines," Indian Journal of Heterocyclic Chemistry 4 (1):67-68 (1994).
Kothari et al., "A Facile One Pot Conversion of 3, 5-dibromo-4-hydroxy Substituted Chalcones to Pyrimidine Derivatives and Their Antibacterial and Herbicidal Activity," Indian Journal of Heterocyclic Chemistry 8(4):285-288 (1999).
Kowalewski et al., "Unfused Heterobicycles as Amplifiers of Phleomycin, IV. 4,5-Bipyrimidines with Dimethylamino and/or Dimethylaminoethylamino Substituents," Australian Journal of Chemistry 34(12):2929-2933 (1981).
Li et al., "PIK3CA Mutations in Breast Cancer Are Associated with Poor Outcome," Breast Cancer Research and Treatment 96(1):91-95 (Mar. 2006).
Mamaev et al., "Reaction Kinetics of Substituted 2-Chloropyrimidines with Piperidine," Reaktsionnaya Sposobnost Organicheskikh Soedinenii 5(3):824-837 (1968).
Mikhaleva et al., Pyrimidines. 70. Relative Reactivity of the Chlorine Atoms of 2,2', 4-Trichloro-4,5-bipyrimidine in the Reaction with Piperidine, Khimiya Geterotsiklicheskikh Soedinenii 6:821-826 (1979).
Mokrosz et al., "Stucture-Activity Relationship Studies of CNS Agents. Part 25:4,6-Di(hyteroaryl)-2-(N-methylpiperazino)pyrimidines as New, Potent 5-HT2A Recepto Ligands: A Verification of the Topographic Model," Archiv der Pharmazie 328(9):659-666 (1995).
Nahta et al., "Signal Transduction Inhibitors in the Treatment of Breast Cancer," Current Medicinal Chemistry—Anti-Cancer Agents 3(3):201-216 (May 2003).
Ouf et al., "Preparation of Some Methyl Pyrimidines Expected to Be Antimetabolites," Egyptian Journal of Pharmaceutical Science 14(2):180-195 (1973).
Sharma et al., "A Convenient One-Pot Synthesis of 2-Substituted-4,6-diaryl Pyrimidines," Indian Journal of Chemistry 38B:966-968 (Aug. 1999).
Balant et al., "Metabolic Considerations in Prodrug Design," Burger's Medicinal Chemistry and Drug Discovery 1:975-977 (1995).
Banker et al., Modern Pharmaceutics 451-596 (1996).
Bennet et al., Cecil Textbook of Medicine, 20th ed., W.B. Saunders, Philadelphia 1996, Parg XIV, Oncology, pp. 1004-1101.
Brown et al., "Some Heterocyclic Analogues of Stilbenes," Journal of the Chemical Society pp. 2147-2153 (1948).

(56) References Cited

OTHER PUBLICATIONS

Bundy et al., "Synthesis of 2, 4-Diaminopyrrolo [2,3-d]pyrimidines Via Thermal Fischer Indolization, Pyrazole Formation With Ytterbium Triflate Catalysis," Journal of Heterocyclic Chemistry 37:1471-1477 (Nov.-Dec. 2000).
Bundy et al., "Synthesis of Novel 2,4-Diaminopyrrolo[2,3-d] pyrimidines with antioxidant, neuroprotective, and Antiasthma Activity," Journal of Medicinal Chemistry 38(21):4161-4163 (Oct. 1995).
Cabaj et al., "Bromine-Mediated Addition of Nucleophiles to the Electon-Rich Pyrimidine Subunit of Tirilazad," Journal of Organic Chemistry 59(17):5090-5092 (Aug. 1994).
Caine et al., "Coagulopathic Complications in Breast Cancer," Cancer 98(8):1578-1586 (Oct. 2003).
Crowder et al., "Treating Breast Cancer Through Novel Inhibitors of the Phosphatidulinositol 3'-Kinase Pathway," Breast Cancer Resaerch 7(5):212-214 (Oct. 2005).
Falco et al., "2,4-Diaminopyrimidines. A New Series of Antimalarials," British Journal of Pharmacology and Chemotherapy 6(2):185-200 (Jun. 1951).
Font et al., "Development of an Efficient and Straightforward Methodology Toward the Synthesis of Molecularly Diverse 2,6-Disubstituted 3,4-Dihydropyrimidin-4(3H)-ones," Synthesis 13:1833-1842 (Sep. 2002).
Ali et al., "Essential role for the p110delta phosphoinositide 3-kinase in the allergic response" Nature 431:1007-1011 (Oct. 21, 2004).
Clayton et al., "A Crucial Role for the p110delta Subunit of Phosphatidylinositol 3-Kinase in B Cell Development and Activation", J. Exp. Med., 196(6):753-763 (Sep. 16, 2002).
Jackson et al., "PI 3-kinase p110beta: a new target for antithrombotic therapy," Nature Medicine 11(5):507-514 (May 2005).
Jou et al., "Essential, Nonredundant Role for the Phosphoinositide 3-Kinase p110delta in Signaling by the B-Cell Receptor Complex," Molecular and Cellular Biology 22(24):8580-8591 (Dec. 2002).
Reif et al., "Cutting Edge: Differential Roles for Phosphoinositide 3-Kinases, p110gamma and p110delta, in Lymphocyte Chemotaxis and Homing," J. Immunol 173:2236-2240 (2004).
Adrisano et al., Pyrimidine. IV, Bollettino Scientifico della Facolta di Chimica Industriale di Bologna 5:48-51 (1947). Volume Date 1944-1947 CA 44:19897, 1950 (1 page).
Golub et al., "Molecular Classification of Cancer: Class Discovery and Class Prediction by Gene Expression Monitoring," Science 286:531-537 (1999).
Lala et al., "Role of nitric oxide in tumor progression: Lessons from experimental tumors," Cancer and Metastasis Reviews 17(1):91-106 (1998).
Buonamici et al., "Interfering with Resistance to Smoothened Antagonists by Inhibition of the PI3K Pathway in Medulioblastoma," Sci Transl Med 2(51):1-8 (2010).
Voskoglou-Nomikos et al., "Clinical Predictive Value of the in Vitro Cell Line, Human Xenograft, and Mouse Allograft Preclinical Cancer Models," Clinical Cancer Research 9:4227-4239 (2003).
Amine et al., "Utilities of 4-(4'Benzyl Phenyl) -6-Arylpyrimidine-2-Thiones for the Synthesis of Biologically Active Condensed and Non-Condensed Heterocycles", Egypt. J. Chem., 41(1-6):267-276 (1998).
Angelo et al., "Synthesis and Antifilarial Activity of N-[4-[[4-Alkoxy-3-[(dialkylamino)methyl]phenyl]amino]-2-pyrimidinyl]-N'-phenylguanidines", J. Med. Chem. 26:1258-1267 (1983).
Essawy et al., "Some Reactions of 4-(2-Methoxynaphthyl)-6-(P-Chlorophenyl) Pyrimidin-2 (1H)-One and its Corresponding 2-Chloro Derivative", Egypt. J. Chem. 37(4):413-421 (1994).
Kidwai et al., "Base Catalysed Pyrimidine Synthesis Using Microwave", Bulletin of the Korean Chemical Society, 24 (11):1575-1578 (2003), CAPLUS Abstract 2003:973238.

Mikhaleva et al., "Pyrimidines. 70. Relative Reactivities of the Chlorine Atoms of 2,2',4-Trichloro-4',5-Dipyrimidinyl in its Reaction with Piperdine", Chemistry of Heterocyclic Compounds (A Translation of Khimiyageterotsiklicheskikh Soedinenii), Plenum Press Co., New York, NY, US, 15(6):671-676 (Jun. 1979).
Jaworska et al., Review of Methods for Assessing the Applicability Domains of SARS and QSARS, "SAR applicability domain" pp. 1-8 (Sep. 27, 2004).
Wolff et al., Burger's Medicinal Chemistry and Drug Discovery, 5th ed. vol. 1, Wiley, New York, 1995, pp. 975-977.
Amary et al., Ollier disease and Maffucci syndrome are caused by somatic mosaic mutations of IDH1 and IDH2. Nat Genet. Nov. 6, 2011;43(12):1262-5.
Balss et al., Analysis of the IDH1 codon 132 mutation in brain tumors. Acta Neuropathol. Dec. 2008;116(6):597-602. Epub Nov. 5, 2008.
Chen et al, Activation of the mammalian target of rapamycin signalling pathway in epidermal tumours and its correlation with cyclin-dependent kinase 2. British Journal of Dermatology Aug. 2009; 160, pp. 442-445.
Dang et al., Cancer-associated IDH1 mutations produce 2-hydroxyglutarate. Nature. Dec. 10, 2009;462(7274):739-44.
Dang et al., IDH mutations in glioma and acute myeloid leukemia. Trends Mol Med. Sep. 2010;16(9):387-97. Epub Aug. 5, 2010.
Dario et al, Targeting of the Tumor Suppressor GRHL3 by a miR-21-Dependent Proto-Oncogenic Network Results in PTEN Loss and Tumorigenesis. Cancer Cell Nov. 2011; 20(5): 635-648.
Gaal et al., Isocitrate dehydrogenase mutations are rare in pheochromocytomas and paragangliomas. J Clin Endocrinol Metab. Mar. 2010;95(3):1274-8. Epub Nov. 13, 2009.
Gross et al., Cancer-associated metabolite 2-hydroxyglutarate accumulates in acute myelogenous leukemia with isocitrate dehydrogenase 1 and 2 mutations. J Exp Med. Feb. 15, 2010;207(2):339-44. Epub Feb. 8, 2010.
Hayden et al., Frequent IDH1 mutations in supratentorial primitive neuroectodermal tumors (sPNET) of adults but not children. Cell Cycle. Jun. 1, 2009;8(11):1806-7. Epub Jun. 30, 2009.
Kranendijket et al., IDH2 mutations in patients with D-2-hydroxyglutaric aciduria. Science. Oct. 15, 2010;330(6002):336. Epub Sep. 16, 2010.
Ming et al, UVB-induced ERK/AKT-dependent PTEN suppression promotes survival of epidermal keratinocytes. Jan. 2010; 29(4): 492-502.
Pansuriya et al., Somatic mosaic IDH1 and IDH2 mutations are associated with enchondroma and spindle cell hemangioma in Ollier disease and Maffucci syndrome. Nat Genet. Nov. 6, 2011;43(12):1256-61.
Salasche, Epidemiology of actinic keratoses and squamous cell carcinoma. J Am Acad Dermatol Jan. 2000;42:S4-7.
Sellner et al., Increased levels of 2-hydroxyglutarate in AML patients with IDH1-R132H and IDH2-R140Q mutations. Eur J Haematol. Nov. 2010;85(5):457-9.
Shibata et al., Mutant IDH1 confers an in vivo growth in a melanoma cell line with BRAF mutation. Am J Pathol. Mar. 2011;178(3):1395-402.
Tani et al., 2,4,6-Trisubstituted pyrimidines. JP 49021148. May 30, 1974.
Pearce et al., Failure modes in anticancer drug discovery and development, Cancer Drug Design and Discovery Edited by Stephen Neidle, Chapter 18, pp. 424-435 (2008).
Johnson et al., British Journal of Cancer, 64(10):1424-1431 (2001).
Simone, Oncology: Introduction, Cecil Textbook of Medicine, 20th Edition, 1:1004-1010 (1996).
Gura, Science, 278(5340):1041-1042 (1997).

* cited by examiner

OXAZOLIDIN-2-ONE-PYRIMIDINE DERIVATIVE AND USE THEREOF FOR THE TREATMENT OF CONDITIONS, DISEASES AND DISORDERS DEPENDENT UPON PI3 KINASES

This application claims benefit under 35 U.S.C. §119(e) of U.S. Provisional Application No. 61/725,113 filed Nov. 12, 2012; the contents of which is incorporated herein by reference in their entirety.

FIELD OF THE INVENTION

The present invention relates to oxazolidin-2-one substituted pyrimidine compounds that act as PI3K (phosphatidylinositol-3-kinase) inhibitors, as well as pharmaceutical compositions thereof, methods for their manufacture and uses for the treatment of conditions, diseases and disorders dependent on PI3 kinases.

BACKGROUND OF THE INVENTION

The phosphatidylinositol-3-kinases superfamily comprises 4 different PI3K related lipid or protein kinases. Class I, II and III are lipid kinases that differ from their substrate specificities whereas class IV PI3K also called PI3-kinase-related protein kinase (PIKK) are protein kinases. Class I PI3Ks comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., Annu. Rev. Biochem 70:535 (2001)). Aberrant regulation of PI3K, which often increases survival and proliferation through activation of AKT kinase is one of the most prevalent events in human cancer and has been shown to occur at multiple levels (Liu et al., Nat Rev Drug Discov 8:627-644 (2009)). For instance, somatic missense mutations in PIK3CA that activate downstream signaling pathways have been described at significant frequencies in a wide diversity of human cancers (Huang et al., Science 318: 1744-1748 (2007), Zhao & Vogt, Oncogene 27:5486-5496 (2008)). The tumor suppressor gene PTEN, which dephosphorylates phosphoinositides at the 3' position of the inositol ring and in so doing antagonizes PI3K activity, is functionally mutated or deleted in a variety of tumors (Keniry & Parsons, Oncogene 27:5477-5485 (2008)). Some studies indicate that the failure to express PTEN can mediate a shift of signaling dependence from the PI3Kα to the β-isoform (Wee et al, Porc Natl Acad Sci USA 105:13057-13062 (2008)). Therefore, inhibition of both class I PI3K α and β-isoforms can be particularly advantageous in cancers that are deficient in PTEN phosphatase.

Published international patent application WO2007/084786 describes substituted pyrimidine molecules that inhibit PI3K.

It is well established that activation of Akt results in the stimulation of the kinase activity of the mammalian target of rapamycin (mTOR). mTOR is a protein kinase and a member of the class IV PI3K. In mammalian cells, mTOR is found in two distinct protein complexes called mTORC1 and mTORC2. Activation of mTORC1 is dependent on active PI3K and Akt kinases. Regulation of mTORC2 activation is more complex. mTORC2 is responsible for enhancement of Akt kinase activity via phosphorylation of serine residue 473 (Sarbassov et al., Science 307:1098-1101 (2005), Bayascas & Alessi, Mol Cell 18(2):143-145 (2005)). Catalytic inhibition of class I PI3K isoforms concomitant with inhibition of mTOR might therefore represent an additional benefit, potentially introducing a stronger effect on the PI3K-Aid pathway.

Cutaneous squamous cell carcinoma (SCC) represents the second most frequent human skin cancer, commonly preceded by actinic keratosis (AK). The pathogenesis of AK and cutaneous SCC has been associated with chronic UV exposure as one major risk factor (Salasche, J Am Acad Dermatol 42: 4-7 (2000)). An enhanced activity of PI3K/Akt/mTOR pathway has been suggested in a previous study (Chen et al., Br J Dermatol; 160 (2):442-445 (2009)). It has been shown that prolonged UV-B irradiation causes a downregulation of PTEN expression at the mRNA and protein level in human keratinocytes in vitro, promoting their survival and growth (Ming et al., Oncogene; 29(4):492-502 (2010)). Based on recent literature, there is a causal link between chronic UV-irradiation and downregulation of PTEN (Darido et al., Cancer Cell; 20(5):635-648 (2011)). Therefore, cutaneous SCC and AK and chronically sun-damaged skin can all be associated with a deficiency of PTEN expression leading to an activation of the PI3K/Akt/mTOR signaling pathway.

SUMMARY OF THE INVENTION

The invention relates to oxazolidin-2-one substituted pyrimidine compounds of the formula (I) and/or pharmaceutically acceptable salts and/or solvates thereof,

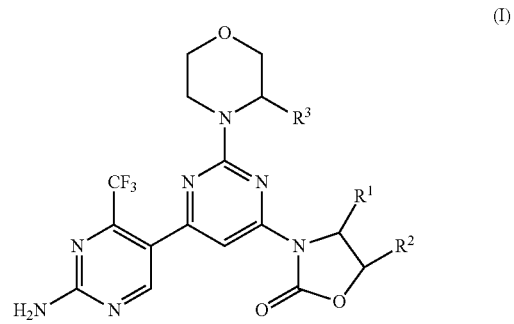

(I)

wherein, $R^1$ is methyl, ethyl or hydroxymethyl;

$R^2$ is phenyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position, or pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position, or a 5 membered monocyclic heteroaryl, containing 2 to 3 heteroatoms selected from N, O or S, which is unsubstituted or substituted by 1 to 2 substituents independently selected from D or F;

and $R^3$ is H or methyl.

Unless specified otherwise, the term "compounds of the present invention" refers to compounds of formula (I) and subformulae thereof, salts of the compound, hydrates or solvates of the compounds and/or salts, as well as all stereoisomers (including diastereoisomers and enantiomers), tautomers and isotopically labeled compounds (including deuterium substitutions). Compounds of the present invention further comprise polymorphs of compounds of formula (I) (or subformulae thereof) and salts thereof. Where compounds of formula (I) are mentioned, this is meant to include also the tautomers and N-oxides of the compounds of formula (I).

The compounds of formula (I) are considered suitable to be used in the treatment of diseases dependent on PI3 kinases. The compounds of formula (I) are considered suitable, for example, to be used in the treatment of diseases dependent on class I PI3 kinase or dependent on class I PI3 kinase and mTOR.

DETAILED DESCRIPTION OF THE INVENTION

The invention may be more fully appreciated by reference to the following description, including the following glossary of terms and the concluding examples. As used herein, the terms "including", "containing" and "comprising" are used herein in their open, non-limiting sense.

The general terms used hereinbefore and hereinafter preferably have within the context of this disclosure the following meanings, unless otherwise indicated:

As used herein, the term "alkoxy" refers to a fully saturated branched, including single or multiple branching, or unbranched hydrocarbon moiety attached to the rest of the molecule via an —O— linking group. Unless otherwise provided, alkoxy refers to moieties having 1 to 16 carbon atoms, 1 to 10 carbon atoms, 1 to 7 carbon atoms, or 1 to 4 carbon atoms. Examples of alkoxy include, but are not limited to, methoxy, ethoxy, n-propoxy, iso-propoxy, n-butyoxy, sec-butoxy, iso-butoxy, tert-butoxy, n-pentoxy, isopentoxy, neopentyl, n-hexyloxy.

As used herein, the term "pyridyl" refers to 2-pyridyl, 3-pyridyl or 4-pyridyl. Substituents in meta or para position are attached to a carbon atom of the pyridyl. A representative example is 3-pyridyl.

As used herein, for substituents on 5 membered monocyclic heteroaryl, containing 2 to 3 heteroatoms selected from N, O or S are attached to a carbon atom of the heteroaryl. Examples of 5 membered monocyclic heteroaryl, containing 2 to 3 heteroatoms selected from N, O or S include, but are not limited to thiazolyl, oxazolyl, 1,2,4-oxadiazolyl, 1,3,4-oxadiazolyl and 1,3,4-thiadiazolyl. A representative example is thiazolyl.

Various embodiments of the invention are described herein. It will be recognized that features specified in each embodiment may be combined with other specified features to provide further embodiments of the present invention.

In one embodiment, the invention provides a compound of the formula (I) and/or a pharmaceutically acceptable salt and/or a solvate thereof, selected from a compound of the formula (Ia)

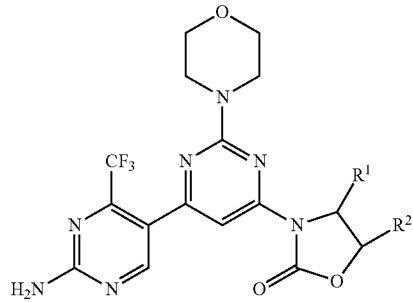

(Ia)

wherein $R^1$ and $R^2$ are as defined for a compound of formula (I) above.

In one embodiment, the invention provides a compound of the formula (I) and/or a pharmaceutically acceptable salt and/or a solvate thereof, selected from a compound of the formula (Ib)

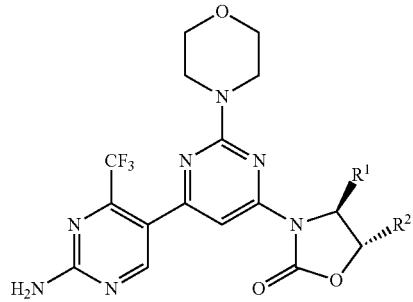

(Ib)

wherein $R^1$ and $R^2$ are as defined for a compound of formula (I) above.

In one embodiment, the invention provides a compound of the formulae (I), (Ia) or (Ib) and/or a pharmaceutically acceptable salt and/or a solvate thereof, wherein
$R^2$ is phenyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (I), (Ia) or (Ib) and/or a pharmaceutically acceptable salt and/or a solvate thereof, wherein
$R^2$ is pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (I), (Ia) or (Ib) and/or a pharmaceutically acceptable salt and/or a solvate thereof, wherein
$R^2$ is a 5 membered monocyclic heteroaryl, containing 2 to 3 heteroatoms selected from N, O or S, which is unsubstituted or substituted by 1 to 2 substituents independently selected from D or F.

In one embodiment, the invention provides a compound of the formulae (I), (Ia) or (Ib) and/or a pharmaceutically acceptable salt and/or a solvate thereof, wherein
$R^2$ is phenyl, 3-methoxy-phenyl, 4-methoxy-phenyl, 4-(3-hydroxypropoxy)-phenyl, 4-(2-hydroxyethoxy)-phenyl or 4-(2-methoxyethoxy)-phenyl.

In another embodiment, the invention provides a compound of the formulae (I), (Ia) or (Ib) and/or a pharmaceutically acceptable salt and/or a solvate thereof, wherein
$R^2$ is 3-pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (I), (Ia) or (Ib) and/or a pharmaceutically acceptable salt and/or a solvate thereof, wherein
$R^2$ is 3-pyridyl.

In another embodiment, the invention provides a compound of the formulae (I), (Ia) or (Ib) and/or a pharmaceutically acceptable salt and/or a solvate thereof, wherein
$R^2$ is thiazolyl, which is unsubstituted or substituted by 1 to 2 substituents independently selected from D or F.

In another embodiment, the invention provides a compound of the formulae (I), (Ia) or (Ib) and/or a pharmaceutically acceptable salt and/or a solvate thereof, wherein
$R^2$ is 2-thiazolyl which is unsubstituted or substituted by 1 to 2 substituents independently selected from D or F.

In another embodiment, the invention provides a compound of the formulae (I), (Ia) or (Ib) and/or a pharmaceutically acceptable salt and/or a solvate thereof, wherein
$R^2$ is 2-thiazolyl.

In one embodiment, the invention provides a compound of the formulae (I), (Ia) or (Ib) and/or a pharmaceutically acceptable salt and/or a solvate thereof, wherein
$R^1$ is methyl.

In another embodiment, the invention provides a compound of the formulae (I), (Ia) or (Ib) and/or a pharmaceutically acceptable salt and/or a solvate thereof, wherein
$R^1$ is ethyl.

In another embodiment, the invention provides a compound of the formulae (I), (Ia) or (Ib) and/or a pharmaceutically acceptable salt and/or a solvate thereof, wherein
$R^1$ is hydroxymethyl.

In one embodiment, the invention provides a compound of the formulae (Ia) or (Ib) and/or a pharmaceutically acceptable salt and/or a solvate thereof, wherein
$R^1$ is methyl;
$R^2$ is phenyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein
$R^1$ is methyl;
$R^2$ is pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein
$R^1$ is methyl;
$R^2$ is a 5 membered monocyclic heteroaryl, containing 2 to 3 heteroatoms selected from N, O or S, which is unsubstituted or substituted by 1 to 2 substituents independently selected from D or F.

In one embodiment, the invention provides a compound of the formulae (Ia) or (Ib) and/or a pharmaceutically acceptable salt and/or a solvate thereof, wherein
$R^1$ is methyl;
$R^2$ is phenyl, 3-methoxy-phenyl, 4-methoxy-phenyl, 4-(3-hydroxypropoxy)-phenyl, 4-(2-hydroxyethoxy)-phenyl or 4-(2-methoxyethoxy)-phenyl.

In another embodiment, the invention provides a compound of the formulae (Ia) or (Ib) and/or a pharmaceutically acceptable salt and/or a solvate thereof, wherein
$R^1$ is methyl;
$R^2$ is 3-pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein
$R^1$ is methyl;
$R^2$ is 3-pyridyl.

In another embodiment, the invention provides a compound of the formulae (Ia) or (Ib) and/or a pharmaceutically acceptable salt and/or a solvate thereof, wherein
$R^1$ is methyl;
$R^2$ is thiazolyl, which is unsubstituted or substituted by 1 to 2 substituents independently selected from D or F.

In another embodiment, the invention provides a compound of the formulae (Ia) or (Ib) and/or a pharmaceutically acceptable salt and/or a solvate thereof, wherein
$R^1$ is methyl;
$R^2$ is 2-thiazolyl which is unsubstituted or substituted by 1 to 2 substituents independently selected from D or F.

In another embodiment, the invention provides a compound of the formulae (Ia) or (Ib) and/or a pharmaceutically acceptable salt and/or a solvate thereof, wherein
$R^1$ is methyl;
$R^2$ is 2-thiazolyl.

In one embodiment, the invention provides a compound of the formulae (Ia) or (Ib) and/or a pharmaceutically acceptable salt and/or a solvate thereof, wherein
$R^1$ is ethyl;
$R^2$ is phenyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein
$R^1$ is ethyl;
$R^2$ is pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein
$R^1$ is ethyl;
$R^2$ is a 5 membered monocyclic heteroaryl, containing 2 to 3 heteroatoms selected from N, O or S, which is unsubstituted or substituted by 1 to 2 substituents independently selected from D or F.

In one embodiment, the invention provides a compound of the formulae (Ia) or (Ib) and/or a pharmaceutically acceptable salt and/or a solvate thereof, wherein $R^1$ is ethyl;

$R^2$ is phenyl, 3-methoxy-phenyl, 4-methoxy-phenyl, 4-(3-hydroxypropoxy)-phenyl, 4-(2-hydroxyethoxy)-phenyl or 4-(2-methoxyethoxy)-phenyl.

In another embodiment, the invention provides a compound of the formulae (Ia) or (Ib) and/or a pharmaceutically acceptable salt and/or a solvate thereof, wherein $R^1$ is ethyl;

$R^2$ is 3-pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein $R^1$ is ethyl;

$R^2$ is 3-pyridyl.

In another embodiment, the invention provides a compound of the formulae (Ia) or (Ib) and/or a pharmaceutically acceptable salt and/or a solvate thereof, wherein $R^1$ is ethyl;

$R^2$ is thiazolyl, which is unsubstituted or substituted by 1 to 2 substituents independently selected from D or F.

In another embodiment, the invention provides a compound of the formulae (Ia) or (Ib) and/or a pharmaceutically acceptable salt and/or a solvate thereof, wherein $R^1$ is ethyl;

$R^2$ is 2-thiazolyl which is unsubstituted or substituted by 1 to 2 substituents independently selected from D or F.

In another embodiment, the invention provides a compound of the formulae (Ia) or (Ib) and/or a pharmaceutically acceptable salt and/or a solvate thereof, wherein $R^1$ is ethyl;

$R^2$ is 2-thiazolyl.

In one embodiment, the invention provides a compound of the formulae (Ia) or (Ib) and/or a pharmaceutically acceptable salt and/or a solvate thereof, wherein $R^1$ is hydroxymethyl;

$R^2$ is phenyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein $R^1$ is hydroxymethyl;

$R^2$ is pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein $R^1$ is hydroxymethyl;

$R^2$ is a 5 membered monocyclic heteroaryl, containing 2 to 3 heteroatoms selected from N, O or S, which is unsubstituted or substituted by 1 to 2 substituents independently selected from D or F.

In one embodiment, the invention provides a compound of the formulae (Ia) or (Ib) and/or a pharmaceutically acceptable salt and/or a solvate thereof, wherein $R^1$ is hydroxymethyl;

$R^2$ is phenyl, 3-methoxy-phenyl, 4-methoxy-phenyl, 4-(3-hydroxypropoxy)-phenyl, 4-(2-hydroxyethoxy)-phenyl or 4-(2-methoxyethoxy)-phenyl.

In another embodiment, the invention provides a compound of the formulae (Ia) or (Ib) and/or a pharmaceutically acceptable salt and/or a solvate thereof, wherein $R^1$ is hydroxymethyl;

$R^2$ is 3-pyridyl, which is unsubstituted or substituted in meta and/or para positions by 1 or 2 substituents independently selected from D, F or methoxy for the meta position and from D, F, methoxy, $C_1$-$C_5$-alkoxy, hydroxy-$C_2$-$C_4$-alkoxy or $C_1$-$C_2$-alkoxy-$C_2$-$C_4$-alkoxy for the para position.

In another embodiment, the invention provides a compound of the formulae (Ia) or (Ib) and/or a pharmaceutically acceptable salt and/or a solvate thereof, wherein $R^1$ is hydroxymethyl;

$R^2$ is 3-pyridyl.

In another embodiment, the invention provides a compound of the formulae (Ia) or (Ib) and/or a pharmaceutically acceptable salt and/or a solvate thereof, wherein $R^1$ is hydroxymethyl;

$R^2$ is thiazolyl, which is unsubstituted or substituted by 1 to 2 substituents independently selected from D or F.

In another embodiment, the invention provides a compound of the formulae (Ia) or (Ib) and/or a pharmaceutically acceptable salt and/or a solvate thereof, wherein $R^1$ is hydroxymethyl;

$R^2$ is 2-thiazolyl which is unsubstituted or substituted by 1 to 2 substituents independently selected from D or F.

In another embodiment, the invention provides a compound of the formulae (Ia) or (Ib) and/or a pharmaceutically acceptable salt and/or a solvate thereof, wherein $R^1$ is hydroxymethyl;

$R^2$ is 2-thiazolyl.

Specific embodiments are provided by the specific exemplified compounds described herein.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Unless indicated otherwise, any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$, detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by class I PI3 kinase, or (i) associated with class I PI3 kinase activity, or (iii) characterized by activity (normal or abnormal) of class I PI3 kinase; or (2) reduce or inhibit the activity of class I PI3 kinase. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of class I PI3 kinase.

In another embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by class I PI3 kinase and mTOR, or (i) associated with class I PI3 kinase and mTOR activity, or (iii) characterized by activity (normal or abnormal) of class I PI3 kinase and mTOR; or (2) reduce or inhibit the activity of class I PI3 kinase and mTOR. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of class I PI3 kinase and mTOR.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Compounds of the present invention may be synthesized by synthetic routes that include processes analogous to those well-known in the chemical arts, particularly in light of the description contained herein. The starting materials are generally available from commercial sources or are readily prepared using methods well known to those skilled in the art (e.g., prepared by methods generally described in Louis F. Fieser and Mary Fieser, Reagents for Organic Synthesis, volumes 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction scheme depicted below provides potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., hydroxyl groups) of intermediates may be necessary. The need for such protection will vary depending on the nature of the remote functionality and the conditions of the preparation methods. Suitable hydroxyl protecting groups include trialkylsilyl ethers where one or two of the alkyl groups can be replaced by phenyl. The need for such protection is readily determined by one skilled in the art. For a general description of protecting groups and their use, see T. W. Greene, Protective Groups in Organic Synthesis, John Wiley & Sons, New York, 1991.

Typically, the compounds of formula (I) can be prepared according to the methods provided infra.

Scheme 1

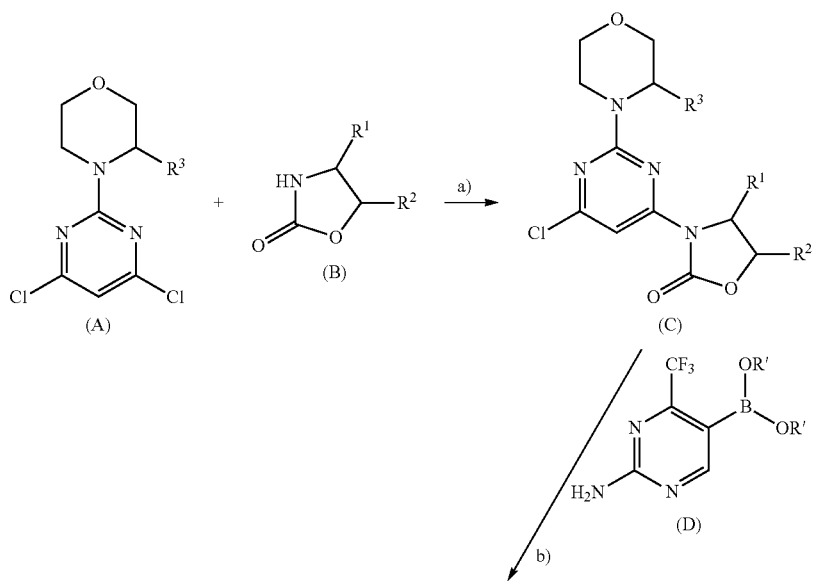

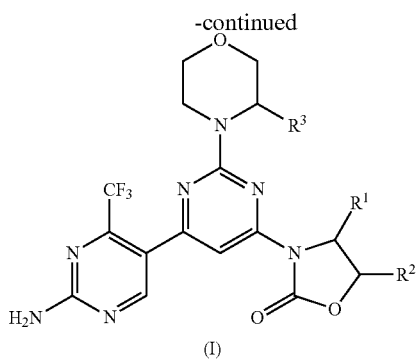

(I)

In one embodiment, the invention relates to a process for manufacturing a compound of formula (I) (Method A) comprising steps a and b.

The compound of formula (I) is obtained via the step a) of coupling the compound of formula (A), wherein $R^3$ is as defined for a compound of formula (I) above

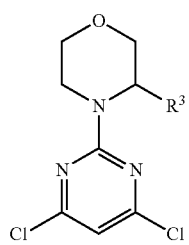

(A)

with a compound of formula (B), wherein $R^1$ and $R^2$ are as defined for a compound of formula (I) above,

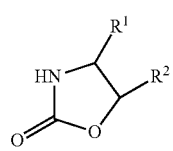

(B)

to form a compound of formula (C), wherein $R^1$, $R^2$ and $R^3$ are as defined for a compound of formula (I) above,

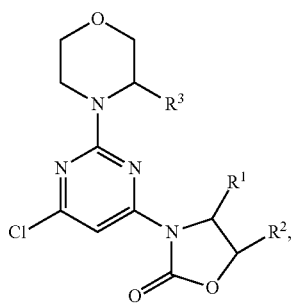

(C)

followed by step b) of coupling the compound of formula (C) with a compound of formula (D), wherein —B(OR')$_2$ represents a cyclic or acyclic boronic acid or boronic acid derivative, such as pinacolato-boron,

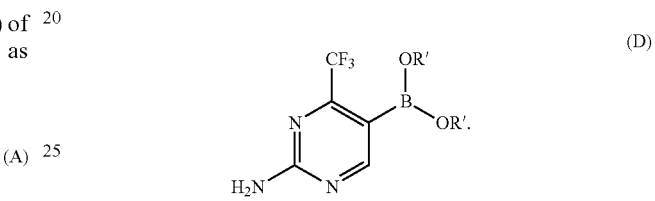

(D)

In cases where a protecting group is present a deprotection step is added to convert protected compound of formula (I) into compound of formula (I).

Step a) is carried out in the presence of a base such as NaH. The reaction is carried out in the presence of an organic solvent such as DMF at temperatures from 0 to 80° C. for 20 to 30 min. Alternatively, the reaction can be carried out under customary Buchwald-Hartwig conditions using a ligand such as Xantphos, X-Phos or 2-di-t-butylphosphino-2'-(N,N-dimethylamino)biphenyl with a palladium catalyst such as Pd$_2$(dba)$_3$ or Pd$_2$(dba)$_3$.CHCl$_3$ or Pd(OAc)$_2$, preferably Pd$_2$(dba)$_3$ with Xantphos, in the presence of a base such as preferably Cs$_2$CO$_3$ or tert-BuONa, in an organic solvent such as an ether, preferably dioxane or THF. The reaction is preferably stirred at a temperature of approximately 80-120° C. The reaction is preferably carried out under an inert gas such as nitrogen or argon. Typical reaction conditions known in the field for Buchwald-Hartwig reactions may be applied to the present process.

Step b) is carried out in the presence of a catalyst, such as a Pd(0) catalyst, e.g. PdCl$_2$(dppf)-CH$_2$Cl$_2$, optionally in the presence of one or more reaction aids, such as a base, e.g. an aqueous base, such as aqueous Na$_2$CO$_3$, optionally in the presence of one or more diluents, particularly polar solvents, e.g. DME. The reaction is stirred at a temperature of approximately 80-120° C. The reaction may be carried out under an inert gas such as nitrogen or argon. Typical reaction conditions known in the field for Suzuki reactions may be applied to the present process.

Alternatively, compounds of formula (I) can also be synthesized by inverting the steps a) and b) shown in Scheme 1 (Method B).

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier.

The pharmaceutical composition can be formulated for particular routes of administration such as topical administration; enteral administration such as for example oral or rectal administration; and parenteral administration such as for example intravenous, intra-muscular or subcutaneous administration. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be prepared according to methods known in the art. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Suitable compositions for topical application, e.g., to the skin and eyes, include aqueous solutions, suspensions, ointments, creams, gels, powders, oils or sprayable formulations, e.g., for delivery by aerosol or the like. Such topical delivery systems will in particular be appropriate for dermal application, e.g., for use in creams, lotions, sprays and the like. They are thus particularly suited for use in topical, including cosmetic, formulations well-known in the art. Such may contain solubilizers, stabilizers, tonicity enhancing agents, buffers and preservatives etc., As used herein a topical application may also pertain to an inhalation or to an intranasal application e.g., to the respiratory system. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

In the context of the present invention, application preferably refers to topical application such as epicutaneous application in a suitable composition comprising a compound of the present invention, or a pharmaceutically acceptable salt thereof, and a pharmaceutically dermatologically acceptable carrier. Suitable compositions for epicutaneous application may comprise all pharmaceutical forms normally utilized for this route of administration and are well-known in the art including solutions, gels, lotions, suspensions, creams, powders, oils, ointments, foams, mousses, emulsions, microemulsions, milks, serums, aerosols, sprays, dispersions, microcapsules, vesicles and microparticles thereof. These compositions are formulated according to conventional techniques.

As used herein, the term "dermatologically acceptable carrier", is a carrier which is suitable for topical application to the keratinous tissue, has good aesthetic properties, is compatible with the active agents of the present invention and any other components, and will not cause any untoward safety or toxicity concerns.

The dermatologically acceptable carrier can be in a wide variety of forms. For example, emulsion carriers, including, but not limited to, oil-in-water, water-in-oil, water-in-oil-in-water, and oil-in-water-in-silicon emulsions, are useful herein. As will be understood by the skilled artisan, a given component will distribute primarily into either the water or oil/silicon phase, depending on the water solubility/dispersibility of the component in the composition.

The composition suitable for epicutaneous application, if desired, can contain various known additives such as excipients, binders, lubricants, and disintegrants. If desired, it can also contain oily materials such as various fats, oils, waxes, hydrocarbons, fatty acids, higher alcohols, ester oils, metallic soaps, animal or vegetable extracts, hydrophilic or lipophilic gelling agents, hydrophilic or lipophilic active agents, other components such as vitamins, amino acids, surfactants, colorants, dyes, pigments, fragrances, odor absorbers, antiseptics, preservatives, bactericides, humectants, thickeners, solvents, fillers, antioxidants, sequestering agents, sunscreens, and the like and combinations thereof, as would be known to those skilled in the art, as long as these are compatible with the active ingredient.

Examples of suitable oils includes mineral oils, plant oils such as peanut oil, sesame oil, soybean oil, safflower oil, sunflower oil, animal oils such as lanolin or perhydrosqualene, synthetic oils such as purcellin oil, silicone oils such as cyclomethicome among others. Fatty alcohols, fatty acids such as stearic acid and waxes such as paraffin wax, carnauba wax or beeswax may also be used as fats.

The composition may also contain emulsifying agents, solvents, hydrophilic gelling agents, lipophilic gelling agents, fatty acid metal salts, hydrophilic acting agents or lipophilic active agents.

The compounds of formula (I) in free form or in salt form, exhibit valuable pharmacological properties, e.g. PI3 kinase modulating properties such as class I PI3 kinase (class I PI3K's) modulating properties or PI3K's modulating properties in conjunction with mTOR modulating properties, e.g. as indicated in in vitro and in vivo tests as provided in the Experimental section, and are therefore indicated for therapy or for use as research chemicals, e.g. as tool compounds.

The compounds of formula (I) in free form or in salt form, are useful in the treatment of class I PI3 kinase dependent diseases, especially diseases depending on class I PI3K α and β-isoforms, as well as diseases depending on class I PI3 kinases, especially diseases depending on class I PI3K α and β-isoforms, in conjunction with mTOR.

Compounds that inhibit the activity of class I PI3K α and β-isoforms, in particular compounds that are substantially equipotent on class I PI3K α and β-isoforms and optionally as well inhibit the activity of mTOR, are considered to be of benefit because such compounds are considered to have the ability to avoid adaption mechanisms due to pathway rewiring through the other isoforms, compared to compounds with unique specificity, e.g. specificity for one member of the class I PI3K family. By "equipotent", it is meant that the compounds inhibit several isoforms to a comparable extent, e.g. as measured in an enzyme or cellular assay described herein.

Suitably, the compounds of formula (I) show sufficient photostability in order to ensure and maximize activity of the compounds of formula (I) when administered epicutaneously to minimize potential irritation and side effects due to degradation products generated. Compounds with superior photostability will simplify technical development and supply due to minimized risks of photodegradation. Suitably, the compounds of formula (I) show good potency in cellular assays using human cell lines derived from cutaneous squamous cell carcinoma. Preferred compounds should demonstrate the ability to penetrate well into skin.

Compounds of the invention may be useful in the treatment of an indication selected from but not limited to non-melanoma skin cancers such as basal cell carcinoma and squamous cell carcinoma; their pre-malignant stages such as actinic keratosis, solar keratosis and chronically sun damaged skin; and other hyperproliferative skin disorders caused by dysregulation of skin fibroblasts such as skin fibrosis, scleroderma, hypertrophic scars or keloids. The compounds of the invention may be particularly useful in the treatment of an indication selected from but not limited to non-melanoma skin cancers.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

In certain instances, it may be advantageous to administer the compound of the present invention in combination with at least one additional pharmaceutical (or therapeutic) agent (e.g., an anti-proliferative or anti-cancer agent or adjunct therapy typically used in chemotherapy). The compound of the present invention may be administered either simultaneously with, or before or after, one or more other therapeutic agent(s).

Alternatively, the compound of the present invention may be administered separately, by the same or different route of administration, or together in the same pharmaceutical composition as the other agent(s).

In one embodiment, the invention provides a product comprising a compound of formula (I) and at least one other therapeutic agent as a combined preparation for simultaneous, separate or sequential use in therapy. In one embodiment, the therapy is the treatment of a disease or condition dependent on PI3 kinases. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

Accordingly, the invention provides the use of a compound of formula (I) for treating a disease or condition mediated by PI3 kinases, wherein the medicament is prepared for administration with another therapeutic agent. The invention also provides the use of another therapeutic agent for treating a disease or condition mediated by PI3 kinases, wherein the medicament is administered with a compound of formula (I).

The invention also provides a compound of formula (I) for use in a method of treating a disease or condition mediated by class I PI3 kinase or mediated by class I PI3 kinase and mTOR, wherein the compound of formula (I) is prepared for administration with another therapeutic agent. The invention also provides another therapeutic agent for use in a method of treating a disease or condition mediated by class I PI3 kinase or mediated by class I PI3 kinase and mTOR, wherein the other therapeutic agent is prepared for administration with a compound of formula (I). The invention also provides a compound of formula (I) for use in a method of treating a disease or condition mediated by class I PI3 kinase or mediated by class I PI3 kinase and mTOR, wherein the compound of formula (I) is administered with another therapeutic agent. The invention also provides another therapeutic agent for use in a method of treating a disease or condition mediated by class I PI3 kinase or mediated by class I PI3 kinase and mTOR, wherein the other therapeutic agent is administered with a compound of formula (I).

The invention also provides the use of a compound of formula (I) for treating a disease or condition mediated by class I PI3 kinase or mediated by class I PI3 kinase and mTOR wherein the patient has previously (e.g. within 24 hours) been treated with another therapeutic agent. The invention also provides the use of another therapeutic agent for treating a disease or condition mediated by class I PI3 kinase or mediated by class I PI3 kinase and mTOR, wherein the patient has previously (e.g. within 24 hours) been treated with a compound of formula (I).

In one embodiment, the other therapeutic agent is selected from therapeutic agents suitable for the treatment of non-melanoma skin cancers such as basal cell carcinoma and squamous cell carcinoma; their pre-malignant stages such as actinic keratosis, solar keratosis and chronically sun damaged skin. Suitably, these other therapeutic agents can be selected from immunostimulatory compounds for example Toll-like receptor agonists such as imiquimod (Aldara®), or from anti-inflammatory agents such as diclofenac (Solaraze®).

The pharmaceutical composition or combination of the present invention can be in unit dosage of about 1 to about 1000 mg of active ingredient(s) for a subject of about 50 to about 70 kg, or about 1 to about 500 mg or about 1 to about 250 mg or about 1 to about 150 mg or about 0.5 to about 100 mg, or about 1 to about 50 mg of active ingredients. Unit dosage can also be of about 50 to about 1000 mg of active ingredient(s) for a subject of about 50 to about 70 kg, or about 50 to about 500 mg or about 50 to about 250 mg or about 50 to about 150 mg or about 50 to about 100 mg of active ingredients. The dosage may depend upon the particular dosage form used for delivering the active ingredient(s). In general, the therapeutically effective dosage of a compound, the pharmaceutical composition, or the combinations thereof, is dependent on the species of the subject, the body weight, age and individual condition, the disorder or disease or the severity thereof being treated. The dosage can also depend on the bioavailability of the active ingredient in the species being treated. A physician, pharmacist, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys, pigs, mini-pigs or isolated organs, tissues and preparations thereof. The compounds of the present invention can be applied in vitro in the form of solutions, e.g., aqueous solutions prepared from e.g. 10 mM DMSO stock solution, and in vivo either enterally, parenterally, advantageously intravenously or topically, e.g., as a suspension, in aqueous solution or other solutions, such as e.g. in propylene glycol based solution. The dosage in vitro may range between about $10^{-3}$ molar and about $10^{-9}$ molar concentrations. A therapeutically effective amount in vivo may range depending on the route of administration, between about 0.1 to about 500 mg/kg, or between about 1 to about 100 mg/kg.

EXAMPLES

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), Chem-Impex International, Inc. (Wood Dale, Ill.), and AstraZeneca Pharmaceuticals (London, England).

Abbreviations

The abbreviations used in the following Examples have the corresponding meanings listed below.

AcOH acetic acid
aq aqueous
ax axial
Boc tert-butoxycarbonyl
Brine saturated (at rt) sodium chloride solution
br s broad singlet
$CDCl_3$ deuterated chloroform
$CHCl_3$-d deuterated chloroform
$CH_2Cl_2$ dichloromethane
$CH_3CN$ acetonitrile
conc. concentrated
CsF cesium fluoride
$CuSO_4$ copper sulfate
d doublet
DIPEA di-isopropylethyl amine
DME dimethoxyethane
DMF N,N-dimethylformamide
DMSO dimethylsulfoxide
DMSO-$d_6$ deuterated dimethylsulfoxide
dppf 1,1'-Bis(diphenylphosphino)ferrocene
eq equatorial
ESI-MS electrospray mass spectrometry
$Et_2O$ diethyl ether
EtOH ethanol
EtOAc ethyl acetate
h hour(s)
Hyflo Hyflo Super Cel®
1HNMR proton nuclear magnetic resonance
KOAc potassium acetate
$KHSO_4$ potassium hydrogensulfate
$K_2CO_3$ potassium carbonate
LC-MS liquid chromatography-mass spectrometry
LDA lithiumdiisopropylamine
MeOH methanol
$MgSO_4$ magnesium sulfate
M molar
m multiplet
MS mass spectrometry
min minute(s)
mL milliliter(s)
m.p. melting point
$MgSO_4$ magnesium sulfate
MHz megahertz
N normal
NaHMDS sodium hexamethyldisilazane
NMR nuclear magnetic resonance
$NEt_3$ triethylamine
$Na_2S_2O_3$ sodium thiosulfate
$Na_2SO_4$ sodium sulfate
$Pd_2(dba)_3$ Tris(dibenzylideneacetone)dipalladium(0)
$PdCl_2(dppf)$ 1,1'-Bis(diphenylphosphino)ferrocene-palladium(II)dichloride
$PdCl_2(dppf)$-$CH_2Cl_2$ 1,1'-Bis(diphenylphosphino)ferrocene-palladium(II)dichloride dichloromethane complex
$PPh_3$ triphenyl phosphine
$Pd(PPh_3)_4$ tetrakis(triphenylphosphine)palladium
Pd palladium
qt quintett
Raney-Ni Raney-nickel
RT room temperature
$R_f$ TLC retention factor
Rt retention time
s singlet
$SiO_2$ silica gel
t triplet
TBAF tetrabutylammonium fluoride
TBDPSCl tert-butyldiphenylsilyl chloride
TBME tert-butylmethylether
TFA trifluoroacetic acid
THF tetrahydrofurane
TLC thin layer chromatography
$t_R$ time of retention
UV ultraviolet
UPLC ultra-performance liquid chromatography General Methods 1H-NMR measurements were performed on a Bruker Ultrashield™ 400 (400 MHz), Bruker Ultrashield™ 600 (600 MHz) or a 500 MHz DRX Bruker CryoProbe (500 MHz) spectrometer using or not trimethylsilane as an internal standard. Chemical shifts (d-values) are reported in ppm downfield from tetramethylsilane, coupling constants (J) are given in Hz, spectra splitting pattern are designated as singulet (s), doublet (d), doublet doublet (dd), triplet (t), quadruplet (q), multiplet or more overlapping signals (m), broad signal (br). Solvents are given in parentheses.

TLC were performed with precoated silica gel 60 $F_{254}$ glass plates (Merck, Darmstadt, Germany) using the respective named solvent systems. Visualization was generally done by UV light (254 nm).

LC-MS:
LC-MS-Method 1
Column: Acquity HSS T3, 1.8 µm, 2.1×50 mm;

Eluent: Water (+0.05% formic acid+3.75 mM ammonium acetate): acetonitrile (+0.04% formic acid), from 95:5 to 2:98 in 1.4 min, hold 98% for 0.75 min;
Flow rate/Temperature: 1.0 mL/min at 60° C.
LC-MS-Method 2
Column: Acquity HSS T3, 1.8 µm, 2.1×50 mm;
Eluent: Water (+0.05% formic acid+3.75 mM ammonium acetate): acetonitrile (+0.04% formic acid), from 98:2 to 2:98 in 1.4 min, hold 98% for 0.75 min;
Flow rate/Temperature: 1.2 mL/min at 50° C.
UPLC 1
Column: Acquity UPLC HSS T3 C18, 1.7 µm 2.1×50 mm, Flow: 1.0 mL/min. Gradient: 5% to 100% B in 1.5 min, 100% B for 1 min, A=water+0.1% TFA, B=acetonitrile+0.1% TFA
Detection: 218 nm or 254 nm Synthesis of Boronic Ester Intermediate The boronic ester intermediate used in the preparation of compounds of the present invention is either commercially available or may be prepared as described in the literature, or in an analogous manner, or can be prepared as described hereafter, or in an analogous manner.

Intermediate 1

5-(4,4,5,5-Tetramethyl-1,3,2-dioxaborolan-2-yl)-4-trifluoromethyl)pyrimidin-2-amine

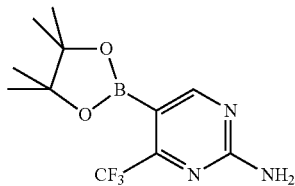 [SMILES: CC1(C)OB(c2cnc(N)nc2C(F)(F)F)OC1(C)C]

a) 5-Bromo-4-trifluoromethyl-pyrimidin-2-ylamine

To a solution of 2-amino-4-trifluoromethylpyrimidine (25 g, 0.15 mol) in $CH_3CN$ (600 mL) was added in the dark a solution of N-bromosuccinimide (34.8 g, 195 mmol) in acetonitrile (200 mL) over a period of 2.5 h. The reaction mixture was stirred for 4.5 h at RT and then concentrated. The residue was dissolved in EtOAc and $H_2O$, the organic solvents were separated, washed with $H_2O$ and brine, dried over $Na_2SO_4$, filtered and concentrated. The residue was purified by column chromatography using EtOAc in hexane from 10% to 40% to provide the title compound as a beige solid (31.2 g, 85%). LC-MS: Rt 0.82 min; (LCMS method 2).

b) 5-(4,4,5,5-Tetramethyl-1,3,2-dioxaborolan-2-yl)-4-(trifluoromethyl)pyrimidin-2-amine To a suspension of 5-Bromo-4-trifluoromethyl-pyrimidin-2-ylamine (16.2 g, 66.3 mmol), bis-pinacolatodiboron (18.5 g, 72.9 mmol) and KOAc (19.5 g, 199 mmol) in dioxane (300 mL) under argon was added $PdCl_2(dppf).CH_2Cl_2$ adduct (2.44 g, 2.98 mmol) and the mixture was stirred for 4 h at 115° C. The reaction mixture was cooled to 50° C. and treated with EtOAc. The resulting suspension was filtered over Hyflo and washed with EtOAc. The combined filtrate was concentrated. The residue was suspended in 2M NaOH, stirred at RT for 5 min and then $Et_2O$ and $H_2O$ were added. The binary mixture was filtered again through Hyflo and the phases were separated. The pH of the resulting aqueous layer was adjusted to 5-6 with 4M aqueous HCl, and the product was extracted with EtOAc. Combined extracts were washed with $H_2O$ and brine, dried over $Na_2SO_4$, filtered and concentrated. The residue was triturated in $Et_2O$/hexane, filtered off and dried to afford the title compound as a light yellow solid (8.33 g, 42%). LC-MS: [M+H] 290.2; Rt 1.00 min; (LCMS method 2).

Synthesis of Oxazolidinone Intermediates

Intermediate 2

(4S*,5S*)-4-Ethyl-5-(4-methoxyphenyl)oxazolidin-2-one

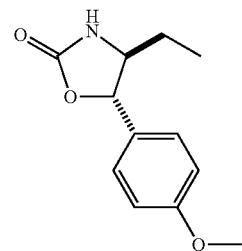 [SMILES: CC[C@@H]1NC(=O)O[C@H]1c1ccc(OC)cc1]

a) (1S*,2S*)-1-(4-Methoxyphenyl)-2-nitrobutan-1-ol

To a solution of $LiAlH_4$ (2 M in THF) (1.84 mL, 3.67 mmol) in dry THF (100 mL), which had been stirred for 30 min at 0° C., was added 1-nitropropane (16.3 mL, 184 mmol) under argon. After 30 min, the 4-methoxybenzaldehyde (4.45 mL, 36.7 mmol) was added in one portion. The mixture was stirred for 6 hours at 0° C. and 18 hours at room temperature. The reaction mixture was quenched with HCl (1M in $H_2O$) and extracted with $CH_2Cl_2$. The organic layers were washed with brine, dried over $MgSO_4$, filtered and concentrated. The residue was purified by column chromatography using $CH_2Cl_2$ in hexane from 0% to 100% to give the title compound (1.4 g, 34%). $^1H$ NMR (600 MHz, DMSO-$d_6$): 7.35 (d, 2H), 6.94 (d, 2H), 5.94 (d, 1 H), 4.80 (dd, 1H), 4.68-4.52 (m, 1H), 3.76 (s, 3H), 1.75-1.69 (m, 1H), 1.25-1.20 (m, 1H), 0.74 (t, 3H).

b) (1S*,2S*)-2-Amino-1-(4-methoxyphenyl)butan-1-ol

A solution of (1S*,2S*)-1-(4-methoxyphenyl)-2-nitrobutan-1-ol (1.0 g, 4.44 mmol) in ethanol (20 mL) was purged with argon, and Pd/C (100 mg, 0.094 mmol) was added at room temperature. The sealed vessel was then purged and refilled with $H_2$ and the reaction mixture was stirred at room temperature for 18 hours. The reaction mixture was filtered over celite, washed with ethanol and concentrated. The residue was purified by column chromatography using $CH_2Cl_2$/MeOH/($NH_4OH$ in $H_2O$) from 100:0:0 to 80:20:1 to yield the title compound as a white solid (450 mg, 51.4%). LC-MS: [M+H] 196.1; Rt 0.44 min; (LCMS method 2).

c) (4S*,5S*)-4-Ethyl-5-(4-methoxyphenyl)oxazolidin-2-one

To a solution of (1S*,2S*)-2-amino-1-(4-methoxyphenyl)butan-1-ol (440 mg, 2.25 mmol) in CH$_2$Cl$_2$ (15 mL) was added under argon NEt$_3$ (0.78 mL, 5.63 mmol) at 0° C. Then diphosgene was added over a period of 5 minutes and the temperature was kept at 0° C. for 30 minutes. The reaction mixture was quenched with ice cold water and a 2 M aqueous solution of Na$_2$CO$_3$, extracted with CH$_2$Cl$_2$, dried over Na$_2$SO$_4$, filtered and concentrated. The residue was triturated with TBME, filtered and dried to give intermediate 2 [(4S*,5S*)-4-ethyl-5-(4-methoxyphenyl)oxazolidin-2-one] as a white powder (220 mg, 44%). LC-MS: [M+H] 222.2; Rt 0.77 min; (LCMS method 2). $^1$H NMR (600 MHz, DMSO-d$_6$): 7.94 (br s, 1H), 7.32 (d, 2H), 6.96 (d, 2H), 5.06 (d, 1H), 3.74 (s, 3H), 3.51 (q, 1H), 1.53 (qt, 2H), 0.85 (t, 3H).

Intermediate 3

(4S*,5S*)-4-Ethyl-5-(3-methoxyphenyl)oxazolidin-2-one

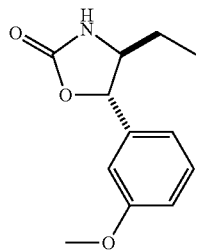 [SMILES: CC[C@@H]1NC(=O)O[C@H]1c1cccc(OC)c1]

The title compound was prepared according to the procedure described for intermediate 2 [(4R*,5R*)-4-ethyl-5-(4-methoxyphenyl)oxazolidin-2-one] to yield intermediate 3 as a colorless oil. LC-MS: [M+H] 222.1; Rt 0.79 min; (LCMS method 2). $^1$H NMR (600 MHz, DMSO-d$_6$): 7.98 (br s, 1H), 7.35-7.29 (m, 1H), 6.83-6.96 (m, 3H), 5.10 (d, 1H), 3.72-3.78 (m, 3H), 3.36-3.29 (m, 1H), 1.49-1.63 (m, 2H), 0.88 (t, 3H).

Intermediate 4

(4S*,5R*)-4-Ethyl-5-phenyloxazolidin-2-one

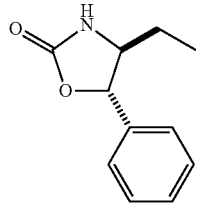

The title compound was prepared according to the procedure described for intermediate 2 [(4R*,5R*)-4-ethyl-5-(4-methoxyphenyl)oxazolidin-2-one] to yield intermediate 4 as a white solid. LC-MS: [M+H] 192.1; Rt 0.77 min; (LCMS method 2)

Intermediate 5:

(4S,5S)-4-Methyl-5-phenyloxazolidin-2-one

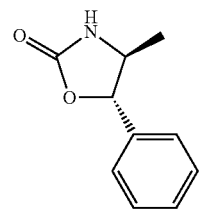

To a solution of (1S,2S)-(+)-Norpseudoephedrine (2.00 g, 13.2 mmol) in CH$_2$Cl$_2$ (60 mL) was added under argon Et$_3$N (4.61 mL, 33.1 mmol) at 0° C. Then, triphosgene (1.57 g, 5.29 mmol) dissolved in 20 mL of CH$_2$Cl$_2$ was added slowly, and the temperature was allowed to warm from 0° C. to room temperature. The reaction mixture was stirred for 4 hours at room temperature. The reaction mixture was then quenched by addition of aqueous NH$_4$Cl. The organic layers were separated, dried over MgSO$_4$, filtered, and concentrated. The residue was purified by column chromatography using EtOAc in heptane from 0% to 100% in order to give the desired product (2.10 g, 89%). LC-MS: [M+H] 178.1; Rt 0.67 min; (LCMS method 2). $^1$H NMR (400 MHz, DMSO-d$_6$) 7.88 (br s, 1H), 7.50-7.32 (m, 5H), 5.09 (d, 1H), 3.78-3.62 (m, 1H), 1.26 (d, 3H).

Intermediate 6:

(4S,5R)-4-Ethyl-5-(thiazol-2-yl)oxazolidin-2-one

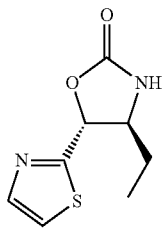

a) (S)-2-(((Benzyloxy)carbonyl)amino)butanoic acid

To a solution of (S)-2-aminobutanoic acid (11.2 g, 109 mmol) in THF (200 mL) and a 2 M aqueous sodium carbonate solution (65.2 ml, 130 mmol) was added dropwise at 0° C. benzyl carbonochloridate (17.06 mL, 119 mmol). After stirring at room temperature for 16 hours, the reaction mixture was extracted with H$_2$O/TBME, the aqueous layer was acidified with HCl (2M in H$_2$O) until pH=2 and extracted with EtOAc. The organic layer was dried over Na$_2$SO$_4$, filtered and the filtrate was concentrated to give the title compound (22.8 g, 77%) as a colorless oil. The product was used in the next step without further purification. LC-MS: [M−H] 236.2; Rt 0.76 min; (LCMS method 1).

b) (S)-Methyl 2-(((benzyloxy)carbonyl)amino)butanoate

To a solution of (S)-2-(((benzyloxy)carbonyl)amino)butanoic acid (10.0 g, 42.1 mmol) in methanol (100 mL) and toluene (300 mL) was added dropwise at room temperature under argon trimethylsilyldiazomethane (23.2 mL, 46.4 mmol). After stirring at room temperature for 1 hour, the reaction mixture was concentrated and the residue was extracted with a solution of EtOAc and brine. The combined organic layers were dried over Na$_2$SO$_4$, filtered and the filtrate was concentrated. The residue was purified by column chromatography (120 g SiO$_2$) using EtOAc in hexane from 0% to 30% in order to give the title compound (5.2 g, 48%) as a colorless oil. LC-MS: [M+H] 252.1; Rt 0.93 min; (LCMS method 1).

c) (S)-Benzyl(1-oxobutan-2-yl)carbamate

To a solution of (S)-methyl 2-(((benzyloxy)carbonyl)amino)butanoate (2.0 g, 7.96 mmol) in toluene (50 mL) was added dropwise at −78° C. under argon DIBAL-H (1M in toluene) (15.9 mL, 15.9 mmol) over a period of 20 minutes and the reaction mixture was stirred at −78° C. for 1 hour. The reaction mixture was quenched at −78° C. with aqueous 1.5 M potassium sodium tartrate solution (20 mL), and was allowed to warm to room temperature. The reaction mixture was extracted with a solution of EtOAc and brine. The combined organic layers were dried over Na$_2$SO$_4$, filtered and concentrated. The residue was purified by column chromatography (24 g SiO$_2$) using EtOAc in hexane from 0% to 30% in order to give the title compound (1.18 g, 64%) as a colorless oil. LC-MS: [M+H] 222.2; Rt 1.01 min; (LCMS method 1). $^1$H NMR (400 MHz, CHCl$_3$-cf): 9.61 (s, 1H), 7.27-7.43 (m, 5H), 5.39 (br s, 1H), 5.15 (m, 2H), 4.15 (q, 1H), 1.96-2.11 (m, 1H), 1.64-1.82 (m, 1H), 1.01-0.79 (m, 3H).

d) Benzyl((1R,2S)-1-hydroxy-1-(thiazol-2-yl)butan-2-yl)carbamate

To a solution of (S)-benzyl(1-oxobutan-2-yl)carbamate (1.1 g, 4.97 mmol) in dichloromethane (30 mL) was added dropwise at −30° C. under argon 2-(trimethylsilyl)thiazole (939 μL, 5.97 mmol) over a period of 10 min. Then, the reaction mixture was stirred at −30° C. for 20 minutes, allowed to warm to room temperature and stirred at room temperature for 2 hours. The reaction mixture was then concentrated at 30° C. and dissolved in THF (30 mL). TBAF (1M in THF) (5.97 mL, 5.97 mmol) was added at 0° C. under argon and the reaction mixture was stirred at room temperature for 2 hours. The reaction mixture was concentrated, and the residue was extracted with EtOAc. The combined organic layers were washed with aqueous sodium carbonate, water and brine, dried over Na$_2$SO$_4$, filtered and the filtrate was concentrated. The residue was purified by column chromatography (24 g SiO$_2$) using EtOAc in hexane from 0% to 30% in order to give the title compound (1.18 g, 64%) as a colorless oil. The residue was purified by column chromatography (24 g SiO$_2$) using MeOH in CH$_2$Cl$_2$ hexane from 0% to 4% in order to give the title compound (340 mg, 43%) as a colorless oil. LC-MS: [M+H] 307.5; Rt 0.86 min; (LCMS method 1).

e) (1R,2S)-2-Amino-1-(thiazol-2-yl)butan-1-ol

To a solution of benzyl((1R,2S)-1-hydroxy-1-(thiazol-2-yl)butan-2-yl)carbamate (330 mg, 1.077 mmol) in acetonitrile (25 mL) at 0° C. under argon was added piperidine (0.213 mL, 2.154 mmol) and dropwise iodotrimethylsilane (293 μL, 2.15 mmol) over a period of 5 minutes. Then, the reaction mixture was allowed to warm to room temperature and was stirred at room temperature for 2 hours. To the reaction mixture was added at 0° C. sodium thiosulfate (500 mg), followed by water (0.5 mL), and the reaction mixture was stirred vigorously at 0° C. for 15 minutes. Further 500 mg of sodium thiosulfate was added, and the mixture was diluted with EtOAc (50 mL), dried over Na$_2$SO$_4$, filtered and concentrated. The residue was triturated with EtOAc, filtered, and the filtrate was concentrated to give the title compound (250 mg, 67%) as a yellow oil.

f) (4S,5R)-4-Ethyl-5-(thiazol-2-yl)oxazolidin-2-one

The title compound was prepared from (1R,2S)-2-Amino-1-(thiazol-2-yl)butan-1-ol according to the procedure described for intermediate 2 to yield intermediate 6 (410 mg, 95%) as a brown oil. This product was used in the next reaction step without further purification.

Intermediate 7

4-Ethyl-5-pyridin-3-yl-oxazolidin-2-one

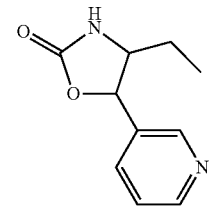

a) 2-Nitro-1-pyridin-3-yl-butan-1-ol

To a solution of LiAlH$_4$ (2M in THF) (0.93 mL, 1.87 mmol) in dry THF (80 mL) at 0° C., was slowly added 1-nitropropane (8.30 mL, 93 mmol) under argon. After 60 min, nicotinaldehyde (2.00 g, 18.7 mmol) was added in one portion. The mixture was stirred for 16 hours, while allowing the temperature to rise from 0° C. to room temperature. The reaction mixture was quenched by addition of 1 mL of 2M aqueous HCl, followed by addition of 4 grams of Na$_2$SO$_4$. The resulting suspension was stirred for 15 minutes and then filtered. The filtrate was concentrated. The residue was purified by column chromatography (40 g SiO$_2$) using EtOAc in hexane from 0% to 100% in order to give the title compound as a white solid (2.6 g, 71%) as a mixture of diastereoisomers A and B. LC-MS: [M+H] 197.1; Rt 0.52 min; (LCMS method 1). A) $^1$H NMR (400 MHz, CHCl$_3$-d): 8.70-8.60 (m, 2H), 7.80-7.74 (m, 1H), 7.42-7.32 (m, 1H), 5.28 (dd, 1H), 4.70-4.58 (m, 1H), 2.97 (d, 1H), 2.29-2.12 (m, 1H), 1.65-1.42 (m, 1H), 0.99 (t, 3H). B) $^1$H NMR (400 MHz, CHCl$_3$-d): 8.70-8.60 (m, 2H), 7.80-7.74 (m, 1H), 7.42-7.32 (m, 1H), 5.15 (dd, 1H), 4.70-4.58 (m, 1H), 2.81 (d, 1H), 1.99-1.85 (m, 1H), 1.65-1.42 (m, 1H), 0.94 (t, 3H).

b) 2-Amino-1-pyridin-3-yl-butan-1-ol

A solution of 2-nitro-1-pyridin-3-yl-butan-1-ol (1.0 g, 4.44 mmol) in ethanol (20 mL) was purged with argon, and 100 mg of Raney-Nickel was added at room temperature. The reaction mixture was three times evacuated and refilled with hydrogen. The reaction was stirred for 16 hours at room temperature. Raney-Nickel was then filtered over Hyflo, and the Hyflo washed with EtOH. The filtrate was then concentrated. The residue was purified by column chromatography (40 g of SiO$_2$) using MeOH in CH$_2$Cl$_2$ from 0% to 100% in order to give the title compound as a yellow oil (180 mg, 21%). LC-MS: [M+H] 167.1; Rt 0.21 min; (LCMS method 1).

c) 4-Ethyl-5-pyridin-3-yl-oxazolidin-2-one

To a solution of 2-amino-1-pyridin-3-yl-butan-1-ol (150 mg, 0.90 mmol) in CH$_2$Cl$_2$ (5 mL) was added under argon NEt$_3$ (314 µL, 5.63 mmol) at 0° C. Then, diphosgene was added over a period of 5 minutes and the temperature was allowed to warm from 0° C. to room temperature within 2 hours. The reaction mixture was quenched with ice cold water and a 2 M solution of Na$_2$CO$_3$, extracted with CH$_2$Cl$_2$, dried over MgSO$_4$, filtered and concentrated. The residue was purified by column chromatography using EtOAc in heptane from 0% to 100% in order to give the title compound (100 mg, 58%) as a mixture of diastereoisomers A and B. LC-MS: [M+H] 193.1; Rt 0.43 min; (LCMS method 1). A) $^1$H NMR (400 MHz, CHCl$_3$-d): 8.70-8.62 (m, 1H), 8.60-8.56 (m, 1H), 7.76-7.71 (m, 1H), 7.42-7.35 (m, 1H), 5.78 (d, 1H), 4.08-3.98 (m, 1H), 1.21-1.05 (m, 2H), 0.84 (t, 3H). B) $^1$H NMR (400 MHz, CHCl$_3$-d): 8.70-8.62 (m, 2H), 7.80-7.76 (m, 1H), 7.42-7.35 (m, 1H), 5.21 (d, 1H), 3.75-3.68 (m, 1H), 1.89-1.69 (m, 2H), 1.05 (t, 3H).

Intermediate 8

4-Methyl-5-pyridin-3-yl-oxazolidin-2-one

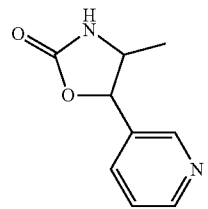

a) 2-Nitro-1-pyridin-3-yl-propan-1-ol

To a solution of LiAlH$_4$ (2M in THF) (1.4 mL, 2.8 mmol) in dry THF (110 mL) at 0° C., was slowly added 1-nitroethane (2.00 mL, 28 mmol) under argon. After 20 min at 0° C., nicotinaldehyde (2.64 mL, 28 mmol) was added in one portion. The mixture was stirred for 16 hours, while allowing the temperature to rise from 0° C. to room temperature. The reaction mixture was quenched by addition of 5 mL of 1M HCl, followed by addition of CH$_2$Cl$_2$ and Na$_2$SO$_4$. The resulting suspension was stirred for 15 minutes and then filtered. The filtrate was concentrated. The residue was then purified by column chromatography (40 g of SiO$_2$) using EtOAc in hexane from 0% to 100% in order to give the product as an oil (3.2 g, 63%) as a mixture of diastereoisomers. LC-MS: [M+H] 183.4; Rt 0.41 min; (LCMS method 1). A) $^1$H NMR (400 MHz, CHCl$_3$-d): 8.58-8.48 (m, 2H), 7.68 (d, 1H) 7.33-7.23 (m, 1H) 5.42-5.38 (m, 1H), 4.70-4.60 (m, 1H), 3.30-2.90 (brs, 1H), 1.46 (d, B) $^1$H NMR (400 MHz, CHCl$_3$-d): 8.58-8.48 (m, 2H), 7.68 (d, 1H) 7.33-7.23 (m, 1H) 5.04 (d, 1H), 4.76-4.69 (m, 1H), 3.30-2.90 (brs, 1H), 1.31 (d, 3H).

b) 4-Methyl-5-pyridin-3-yl-oxazolidin-2-one

A solution of 2-nitro-1-pyridin-3-yl-butan-1-ol (3.20 g, 17.6 mmol) in ethanol (90 mL) was purged with argon, and 200 mg of Raney-Nickel was added at room temperature. The reaction mixture was three times evacuated and refilled with hydrogen. The reaction was stirred for 16 hours under H2 at room temperature. Raney-Nickel was then filtered over Hyflo, and the Hyflo washed with EtOH. The filtrate was then concentrated in order to give 2-amino-1-pyridin-3-yl-propan-1-ol as a product (2.35 g, 88%), which was used in the next reaction step without purification. To a solution of 2-amino-1-pyridin-3-yl-propan-1-ol (700 mg, 4.60 mmol) in CH$_2$Cl$_2$ (20 mL) was added under argon Et$_3$N (1.60 mL, 11.5 mmol) at 0° C., followed by triphosgene (819 mg, 2.76 mmol, dissolved in 5 mL of CH$_2$Cl$_2$). The reaction temperature was allowed to warm from 0° C. to room temperature within one hour. The reaction mixture was then quenched with ice cold water and a 2 M solution of Na$_2$CO$_3$, extracted with CH$_2$Cl$_2$, dried over MgSO$_4$, filtered and concentrated. The residue was purified by column chromatography using EtOAc in hexane from 0% to 100% in order to give the product (160 mg, 20%). LC-MS: [M+H] 179.1; Rt 0.31 min; (LCMS method 1).

Intermediate 9

(4S,5S)-4-((tert-Butyldiphenylsilyloxy)methyl)-5-phenyloxazolidin-2-one

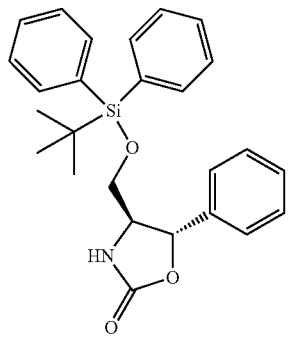 [SMILES: CC(C)(C)[Si](OC[C@@H]1NC(=O)O[C@H]1c1ccccc1)(c1ccccc1)c1ccccc1]

a)
(4S,5S)-4-Hydroxymethyl-5-phenyl-oxazolidin-2-one (1S,2S)-2-Amino-1-phenylpropane-1,3-diol (20.0 g, 120 mmol), diethyl carbonate (29.7 mL, 245 mmol), and K$_2$CO$_3$ (1.65 g, 12.0 mmol) were charged into a flask with mechanical stirrer and a vigreux-column. This suspension was heated in an oil bath at 135° C., to give a yellow solution. The accrued EtOH was distilled off over the vigreux column. The reaction was stirred over a period of 3 h, until no more EtOH could be distilled off. The reaction mixture was then cooled to 50° C., diluted with EtOAc and aqueous NaHCO$_3$. The organic layers were separated, washed with brine, dried over MgSO$_4$, filtered, and concentrated. The residue was purified by column chromatography (550 g SiO$_2$) using EtOAc in heptane from 33% to 100% in order to give the title compound as a beige oil (7.50 g, 33%). $^1$H NMR (400 MHz, DMSO-d$_5$): 7.87 (br s, 1H), 7.50-7.30 (m, 5H), 5.37 (d, 1H), 5.23-5.17 (m, 1H), 3.70-3.60 (m, 1H), 3.60-3.50 (m, 2H).

b) (4S,5S)-4-((tert-Butyldiphenylsilyloxy)methyl)-5-phenyloxazolidin-2-one

To a solution of (4S,5S)-4-hydroxymethyl-5-phenyl-oxazolidin-2-one (3.50 g, 17.2 mmol), NEt$_3$ (4.80 mL, 34.4 mmol), and DMAP (105 mg, 861 µmol) in DMF (20 mL) was added dropwise TBDPSCl (4.86 mL, 18.9 mmol) at room temperature. The reaction was stirred for 3 hours at room temperature. The reaction mixture was then concentrated and diluted with TBME, the organic layers were separated, washed with aqueous NaHCO$_3$ and brine, dried over MgSO$_4$, and concentrated. The residue was purified by column chromatography (120 g SiO$_2$) using EtOAc in heptane from 0% to 60% in order to give the title compound as a white solid (4.28 g, 57%). LC-MS: [M+H] 432.2; Rt 1.36 min; (LCMS method 2).

Intermediate 10

(4S,5S)-4-(((tert-Butyldiphenylsilyl)oxy)methyl)-5-(4-methoxyphenyl)oxazolidin-2-one

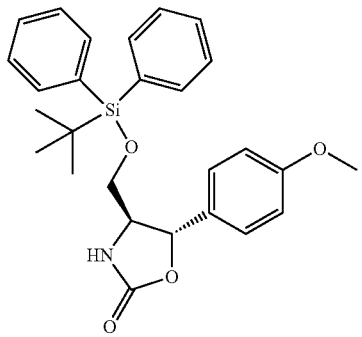 [SMILES: COc1ccc([C@@H]2OC(=O)N[C@H]2CO[Si](c2ccccc2)(c2ccccc2)C(C)(C)C)cc1]

To a solution of (4S,5S)-4-(hydroxymethyl)-5-(4-methoxyphenyl)oxazolidin-2-one [545435-91-4] (0.68 g, 3.05 mmol) and imidazole (0.249 g, 3.66 mmol) in DMF (10 mL) was added dropwise TBDPSCl (0.97 mL, 3.66 mmol) at 0-5° C. The reaction mixture was allowed to warm to RT and was stirred overnight at RT. The reaction mixture was concentrated and the residual oil was dissolved in TBME and washed with 10% aqueous KHSO$_4$, H$_2$O, saturated NaHCO$_3$ solution and brine, dried over MgSO$_4$, filtered and concentrated. The residue was purified by column chromatography using EtOAc in heptane from 5% to 50% in order to give the title compound as a white foam (1.62 g, 55%). TLC (heptane/EtOAc 1:1) R$_f$=0.44; LC-MS: [M+H] 462; Rt 1.36 min; (LCMS method 2). $^1$H NMR (400 MHz, CDCl$_3$): 7.65 (d, 4H), 7.35-7.60 (m, 6H), 7.24 (d, 2H), 6.92 (d, 2H), 5.24 (d, 1H), 5.20 (br s, 1H), 3.84 (m, 4H), 3.77 (m, 2H), 1.09 (s, 9H).

Intermediate 11:

(4S,5S)-4-(((tert-Butyldimethylsilyl)oxy)methyl)-5-(4-(2-methoxyethoxy)phenyl)oxazolidin-2-one

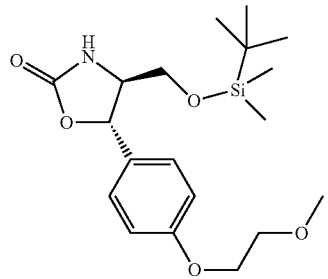 [SMILES: COCCOc1ccc([C@@H]2OC(=O)N[C@H]2CO[Si](C)(C)C(C)(C)C)cc1]

a) (R)-Methyl 2-((tert-butoxycarbonyl)amino)-3-(4-(2-ethoxyethoxy)phenyl)propanoate To a suspension of (R)-methyl 2-((tert-butoxycarbonyl)amino)-3-(4-hydroxyphenyl)-propanoate (4.43 g, 15.00 mmol), K$_2$CO$_3$ (4.15 g, 30.0 mmol) and sodium iodide (112 mg, 750 µmol) in acetonitrile (100 mL) was added 1-bromo-2-methoxyethane (5.64 mL, 60.0 mmol) and the resulting mixture was stirred at reflux for 2 days. The reaction mixture was diluted with TBME and washed with H$_2$O and brine. Combined extracts were dried over MgSO$_4$, filtered and concentrated to provide the title compound as a yellow oil (5.3 g, 95%). TLC (toluene/TBME 2:1) R$_f$=0.44; t$_R$=1.084 min (UPLC 1); LC-MS: [M+H] 354; Rt 1.02 min; (LCMS method 2); $^1$H NMR (400 MHz, CDCl$_3$): δ 7.05 (d, 2H), 6.88 (d, 2H), 4.96 (br d, 1H), 4.58 (m, 1H), 4.12 (dd, 2H), 3.76 (dd, 2H), 3.73 (s, 3H), 3.47 (s, 3H), 3.05 (m, 2H), 1.44 (s, 9H).

b) (4R,5S)-Methyl 5-(4-(2-methoxyethoxy)phenyl)-2-oxooxazolidine-4-carboxylate

To a solution of (R)-methyl 2-((tert-butoxycarbonyl)amino)-3-(4-hydroxyphenyl)-propanoate (5.34 g, 14.35 mmol) in acetonitrile (260 mL) was added under argon a solution of potassium persulfate (7.76 g, 28.7 mmol) in H$_2$O (190 mL) and a solution of CuSO$_4$ (0.458 g, 2.87 mmol) dissolved in H$_2$O (70 mL). The resulting mixture was stirred for 3 h at 70° C. The reaction mixture was extracted with EtOAc. Combined extracts were washed with brine, dried over MgSO$_4$, filtered and concentrated. The residue was purified by column chromatography using EtOAc in heptane from 20% to 100% in order to give the title compound as a yellow oil (2.33 g, 52%). TLC (heptane/EtOAc 1:2) R$_f$=0.19; t$_R$=0.680 min (UPLC 1); LC-MS: [M+H] 296; Rt 0.68 min; (LCMS method 2); $^1$H NMR (400 MHz, CDCl$_3$): 7.36 (d, 2H), 6.99 (d, 2H), 5.86 (br d, 1H), 5.62 (d, 1H), 4.30 (d, 1H), 4.16 (dd, 2H), 3.88 (s, 3H), 3.79 (dd, 2H), 3.48 (s, 3H).

c)(4S,5S)-4-(Hydroxymethyl)-5-(4-(2-methoxy-ethoxy)phenyl)oxazolidin-2-one

To a suspension of (4R,5S)-methyl 5-(4-(2-methoxyethoxy)phenyl)-2-oxooxazolidine-4-carboxylate (2.30 g, 7.79 mmol) in EtOH (45 mL) was added in portions at 0-5° C. sodium borohydride (648 mg, 17.1 mmol). The reaction mixture was stirred for 0.5 h at RT and then acidified with 4M aqueous HCl (10 mL) at 0-5° C. The reaction mixture was concentrated and the product was extracted with EtOAc. Combined extracts were washed with brine, dried over MgSO$_4$, filtered and concentrated to afford the title compound as a beige foam (1.80 g, 81%). $t_R$=0.498 min (UPLC 1); LC-MS: [M+H] 268; Rt 0.55 min; (LCMS method 2); $^1$H NMR (400 MHz, CDCl$_3$): 7.31 (d, 2H), 6.96 (d, 2H), 6.45 (br s, 1H), 5.33 (d, 1H), 5.30 (br s, 1H), 3.75-4.30 (m, 7H), 3.47 (s, 3H).

d) (4S,5S)-4-(((tert-Butyldimethylsilyl)oxy)methyl)-5-(4-(2-methoxyethoxy)phenyl)-oxazolidin-2-one The title compound was prepared in analogy to the procedure described for intermediate 10 [(4S,5S)-4-(((tert-butyldiphenylsilyl)oxy)methyl)-5-(4-methoxyphenyl)oxazolidin-2-one] from (4S,5S)-4-(hydroxymethyl)-5-(4-(2-methoxyethoxy)phenyl)oxazolidin-2-one and TBDMS-Cl to afford after purification by column chromatography (using EtOAc in heptane from 5% to 50%) intermediate 11 as a light yellow oil. TLC (heptane/EtOAc 1:1) R$_f$=0.26; $t_R$=1.28 min (UPLC 1); LC-MS: [M+H] 382.2; Rt 1.17 min; (LCMS method 2); $^1$H NMR (400 MHz, CDCl$_3$): 7.30 (d, 2H), 6.97 (d, 2H), 5.44 (br s, 1H), 5.23 (d, 1H), 4.18 (dd, 2H), 3.70-3.85 (m, 5H), 3.48 (s, 3H), 0.91 (s, 9H), 0.11 (s, Intermediate 12

(4S,5S)-5-(4-(2-((tert-Butyldimethylsilyl)oxy)ethoxy)phenyl)-4-(((tert-butyldimethylsilyl)oxy)methyl)oxazolidin-2-one

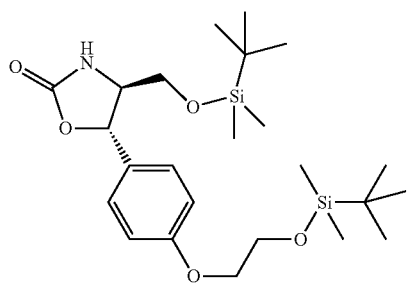 [SMILES: CC(C)(C)[Si](C)(C)OCCOc1ccc([C@@H]2OC(=O)N[C@H]2CO[Si](C)(C)C(C)(C)C)cc1]

The title compound was prepared in analogy to the procedure described for intermediate 11 starting with (R)-methyl 2-((tert-butoxycarbonyl)amino)-3-(4-hydroxyphenyl)propanoate and (2-bromoethoxy)(tert-butyl)dimethylsilane. TLC (heptane/EtOAc 1:1) R$_f$=0.51; $t_R$=1.764 min (UPLC 1); LC-MS: [M+H] 482; Rt 1.57 min; (LCMS method 1); $^1$H NMR (400 MHz, CDCl$_3$): 7.31 (d, 2H), 6.96 (d, 2H), 5.26 (br s, 1H), 5.22 (d, 1H), 4.13 (m, 2H), 4.00 (m, 2H), 3.79 (m, 1H), 3.67 (m, 2H), 0.93 (s, 9H), 0.92 (s, 9H), 0.11 (m, 12H).

Intermediate 13

(4S,5S)-4-(((tert-Butyldimethylsilyl)oxy)methyl)-5-(4-(3-((tert-butyldimethylsilyl)oxy)propoxy)phenyl)oxazolidin-2-one

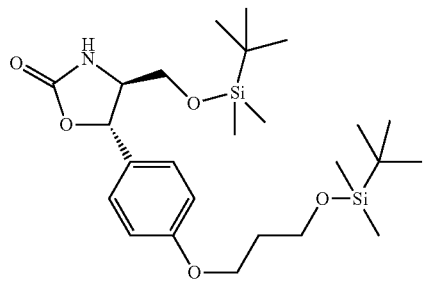 [SMILES: CC(C)(C)[Si](C)(C)OCCCOc1ccc([C@@H]2OC(=O)N[C@H]2CO[Si](C)(C)C(C)(C)C)cc1]

The title compound was prepared in analogy to the procedure described for intermediate 12 starting with (R)-methyl 2-((tert-butoxycarbonyl)amino)-3-(4-hydroxyphenyl)propanoate and (3-bromopropoxy)(tert-butyl)dimethylsilane. TLC (heptane/EtOAc 1:1) R$_f$=0.49; $t_R$=1.832 min (UPLC 1); LC-MS: [M+H] 496; Rt 1.62 min (LC-MS method 1); $^1$H NMR (400 MHz, CDCl$_3$): 7.30 (d, 2H), 6.95 (d, 2H), 5.27 (br s, 1H), 5.22 (d, 1H), 4.13 (dd, 2H), 4.00 (m, 2H), 3.80 (m, 3H), 3.74 (m, 2H), 2.01 (m, 2H), 0.93 (s, 9H), 0.91 (s, 9H), 0.10 (s, 6H), 0.06 (s, 6H).

Intermediate 14

(4S,5R)-4-Methyl-5-thiazol-2-yl-oxazolidin-2-one

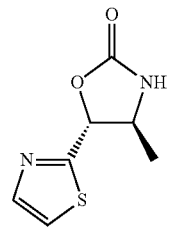

a)(2-Hydroxy-1-methyl-2-thiazol-2-yl-ethyl)-carbamic acid tert-butyl ester

Boc-L-alanal (9.99 g, 57.7 mmol) was dissolved in 200 mL of CH$_2$Cl$_2$. 2-(trimethylsilyl)-thiazole (9.90 g, 62.9 mmol) dissolved in 70 mL of CH$_2$Cl$_2$ was added to the reaction mixture at −20° C. under argon. After 21 hours at −20° C., the reaction mixture was concentrated. The residue was then dissolved in 180 mL of THF, when TBAF (1M in THF, 63.4 mL, 63.4 mmol) was added, and the reaction mixture was stirred for 4 hours at room temperature. The reaction mixture was then concentrated. The residue was purified by column chromatography (120 g SiO$_2$) using EtOAc in hexane from 0% to 100% in order to give the title compound as a diastereomeric mixture (14.0 g, 93%). LC-MS: [M+H] 259.2; Rt 0.78 min; (LCMS method 1).

b) 2-Amino-1-thiazol-2-yl-propan-1-ol

2-Hydroxy-1-methyl-2-thiazol-2-yl-ethyl)-carbamic acid tert-butyl ester (13.8 g, 53.4 mmol) was dissolved in 50 mL of dioxane. 134 mL (534 mmol) of 4M HCl in dioxane was added, and the reaction mixture was stirred for 4 hours at room temperature. The reaction mixture was then concentrated, and the residue was diluted with diethyl ether and filtered in order to gain the title compound as a white salt as a diastereomeric mixture (11.5 g, 92%). LC-MS: [M+H] 159.1; Rt 0.22 min; (LCMS method 1).

c)(4S,5R)-4-Methyl-5-thiazol-2-yl-oxazolidin-2-one

A mixture of diastereoisomers of 2-amino-1-thiazol-2-yl-propan-1-ol (4.20 g, 18.2 mmol) was dissolved in 160 mL of $CH_2Cl_2$. Diisopropylethylamine (11.1 mL, 63.6 mmol) was added at 0° C., followed by triphosgene (2.70 g, 9.09 mmol) dissolved in 40 mL of $CH_2Cl_2$. The reaction mixture was stirred at room temperature for 2 hours and then diluted with $CH_2Cl_2$. The organic solvents were separated, washed with aqueous $NaHCO_3$ and brine, dried over $MgSO_4$, filtered, and concentrated. The residue was purified by column chromatography (80 g $SiO_2$) using EtOAc in hexane from 0% to 100 in order to give the title compound as a single enantiomer (2.16 g, 64%). LC-MS: [M+H] 185.3; Rt 0.45 min; (LCMS method 1). $^1$H NMR (400 MHz, CHCl$_3$-d): 7.75 (d, 1H), 7.35 (d, 1H), 5.60 (br s, 1H), 5.32 (d, 1H), 4.18-4.09 (m, 1H), 1.45 (d, 3H).

Intermediate 15

(4S,5S)-4-Methyl-5-thiazol-2-yl-oxazolidin-2-one

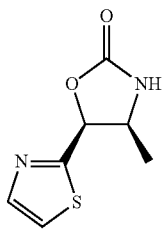

To a mixture of (1S,2S)-2-amino-1-thiazol-2-yl-propan-1-ol and (1R,2S)-2-amino-1-thiazol-2-yl-propan-1-ol (2.9 g, 12.5 mmol) in $CH_2Cl_2$ (40 mL) was added under argon $NEt_3$ (10.5 mL, 75 mmol) at 0° C. Then, triphosgene (1.86 g, 6.27 mmol) dissolved in 40 mL of $CH_2Cl_2$ was added slowly, and the temperature was allowed to warm from 0° C. to room temperature. The reaction mixture was stirred for 16 hours at room temperature. The reaction mixture was then quenched by addition of aqueous $NaHCO_3$. The organic layers were separated, dried over $MgSO_4$, filtered, and concentrated. The residue was purified by column chromatography using EtOAc in heptane from 0% to 100% in order to give the desired product (330 mg, 13%). LC-MS: [M+H] 185.0; Rt 0.48 min; (LCMS method 1). $^1$H NMR (400 MHz, CHCl$_3$-d): 7.79 (d, 1H), 7.34 (d, 1H), 5.91 (d, 1H), 5.71 (br s, 1H), 4.48-4.38 (m, 1H), 0.89 (d, 3H).

Synthesis of Example compounds

Example 1

(4S,5R)-3-(2'-Amino-2-morpholin-4-yl-4'-trifluoromethyl-[4,5]bipyrimidinyl-6-yl)-4-methyl-5-thiazol-2-yl-oxazolidin-2-one

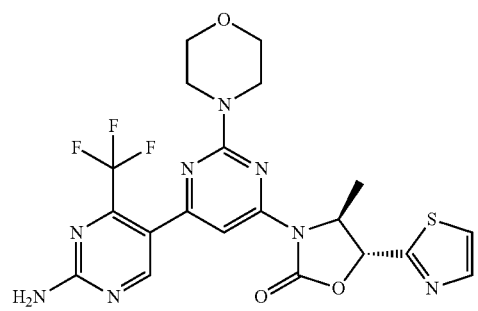 [SMILES: C[C@H]1[C@H](c2nccs2)OC(=O)N1c1cc(-c2cnc(N)nc2C(F)(F)F)nc(N2CCOCC2)n1]

a)(4S,5R)-3-(6-Chloro-2-morpholin-4-yl-pyrimidin-4-yl)-4-methyl-5-thiazol-2-yl-oxazolidin-2-one (4S,5R)-4-Methyl-5-thiazol-2-yl-oxazolidin-2-one (4.70 g, 20.1 mmol) was dissolved in 70 mL of DMF and cooled to 0° C. NaH (964 mg, 60% in oil, 24.1 mmol) was added under argon, and the reaction mixture was stirred for 30 minutes at 0° C. 4-(4,6-dichloropyrimidin-2-yl)morpholine (3.70 g, 20.1 mmol) dissolved in 30 mL of DMF was added, and the reaction mixture was stirred for 3 hours at 0° C., followed by stirring at RT for 2 hours. The reaction was then quenched by addition of aqueous $NH_4Cl$, followed by dilution with EtOAc; the organic solvents were separated, washed with brine, dried over $MgSO_4$, filtered, and concentrated. The residue was purified by column chromatography (80 g $SiO_2$) using EtOAc in hexane from 0% to 100% in order to give the title compound (3.64 g, 48%). LC-MS: [M+H] 382.2, 384.1; Rt 1.10 min; (LCMS method 1). $^1$H NMR (400 MHz, CHCl$_3$-d): 7.77 (d, 1H), 7.38-7.33 (m, 2H), 5.39 (d, 1H), 5.07-4.98 (m, 1H), 3.75-3.55 (m, 8H), 1.64 (d, 3H).

b) (4S,5R)-3-(2'-Amino-2-morpholuoromethyl-[4,5]'pipyrimidinyl-6-yl)-4-met hyl-5-thiazol-2-yl-oxazolidin-2-one To a solution of (4S,5R)-3-(6-chloro-2-morpholin-4-yl-pyrimidin-4-yl)-4-methyl-5-thiazol-2-yl-oxazolidin-2-one (1.30 g, 3.40 mmol) in 20 mL of dimethoxyethane was added under argon 5-(4,4,5,5-tetramethyl-1,3,2-dioxaborolan-2-yl)-4-(trifluoromethyl)pyrimidin-2-amine (1.08 g, 3.75 mmol), $PdCl_2$(dppf)-$CH_2Cl_2$ (214 mg, 262 μmol), and 2 M aqueous sodium carbonate (5.11 mL, 10.2 mmol). The reaction mixture was stirred at 80° C. for 30 minutes. The reaction mixture was then cooled to RT and diluted with 80 mL of EtOAc, the organic solvents were washed with aqueous $NH_4Cl$ and brine, dried over $MgSO_4$, filtered, and concentrated. The residue was purified by column chromatography (80 g $SiO_2$) using EtOAc in hexane from 0% to 100% in order to give example 1 as an amorphous solid (1.20 g, 69%). LC-MS: [M+H] 509.0; Rt 0.99 min; (LCMS method 1). $^1$H NMR (400 MHz, DMSO-d₆): 8.58 (s, 1H), 7.92 (d, 1H), 7.87 (d, 1H), 7.64 (br s, 7.41 (s, 1H), 5.89 (d, 1H), 5.10-5.04 (m, 1H), 3.75-3.55 (m, 8H), 1.62 (d,

Example 2

(4S*,5S*)-3-(2'-amino-2-morpholino-4'-(trifluoromethyl)-[4,5'-bipyrimidin]-6-yl)-4-ethyl-5-(4-methoxyphenyl)oxazolidin-2-one

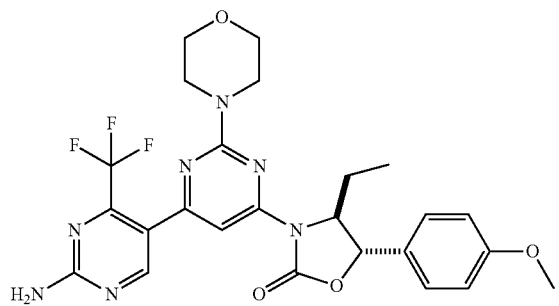 [SMILES: CC[C@H]1[C@H](c2ccc(OC)cc2)OC(=O)N1c1cc(-c2cnc(N)nc2C(F)(F)F)nc(N2CCOCC2)n1]

a)(4S*,5S*)-3-(6-Chloro-2-morpholinopyrimidin-4-yl)-4-ethyl-5-(4-methoxyphenyl)oxazolidin-2-one To a solution of (4R*,5R*)-4-ethyl-5-(4-methoxyphenyl) oxazolidin-2-one (217 mg, 0.98 mmol) in DMF (2 mL) was added at room temperature under argon NaH (51.4 mg, 1.18 mmol). After 20 minutes, a suspension of 4-(4,6-dichloropyrimidin-2-yl)morpholine (230 mg, 0.98 mmol in DMF (1 mL) was added, and the reaction mixture was stirred at 85° C. for 20 minutes. The solution was quenched at 0° C. with aqueous NH₄Cl, extracted with ethyl acetate, and the organic layers were dried over Na₂SO₄, filtered and concentrated. The crude product was purified by column chromatography using EtOAc in hexane from 0% to 20% in order to give the title compound as a white solid (375 mg, 91%). LC-MS: [M+H] 419.1; Rt 1.26 min; (LCMS method 1).

b) (4S*,5S*)-3-(2'-Amino-2-morpholino-4'-(trifluoromethyl)-[4,5'-bipyrimidin]-6-yl)-4-ethyl-5-(4-methoxyphenyl)oxazolidin-2-one To a solution of (4R*,5R*)-3-(6-chloro-2-morpholinopyrimidin-4-yl)-4-ethyl-5-(4-methmphenyl) oxazolidin-2-one in DME (2 mL) was added at room temperature under argon 5-(4,4,5,5-tetramethyl-1,3,2-dioxaborolan-2-yl)-4-(trifluoromethyl)pyrimidin-2-amine (76 mg, 0.26 mmol), a solution of 2M aqueous Na₂CO₃ (0.36 mL, 0.72 mmol) and tetrakis (triphenylphosphine)palladium (27.6 mg, 24 μmol). The mixture was stirred at 80° C. for 1 hour, cooled to RT and concentrated. The residue was purified by column chromatography using EtOAc in hexane from 0% to 20% in order to give the title compound (125 mg, 95%) as a yellow oil. LC-MS: [M+H] 546.2; Rt 1.17 min; (LCMS method 1). ¹H NMR (400 MHz, CHCl₃-d): 8.63 (s, 1H), 7.68 (s, 1H), 7.31 (d, 2H), 6.96 (d, 2H), 5.49 (br s, 2H), 5.27 (d, 1H), 4.66-4.61 (m, 1H), 3.84 (s, 3H), 3.80-3.73 (m, 2.30-2.00 (m, 2H), 1.08 (t, 3H).

Example 3

(4S,5S)-3-(2'-Amino-2-morpholino-4'-(trifluoromethyl)-[4,5'-bipyrimidin]-6-yl)-4-(hydroxymethyl)-5-(4-methoxyphenyl)oxazolidin-2-one

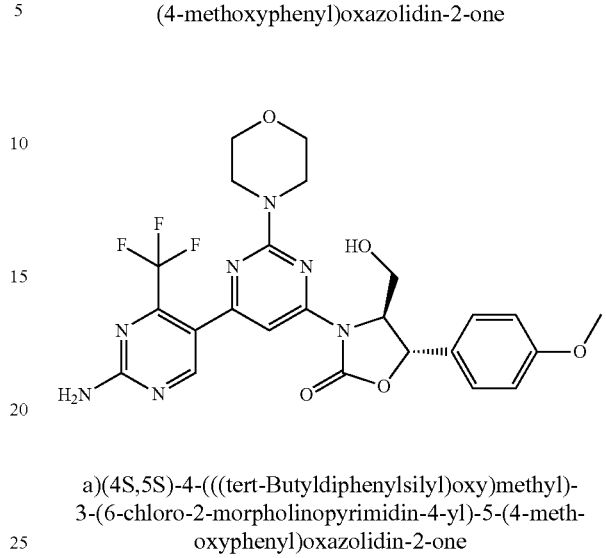

a)(4S,5S)-4-(((tert-Butyldiphenylsilyl)oxy)methyl)-3-(6-chloro-2-morpholinopyrimidin-4-yl)-5-(4-methoxyphenyl)oxazolidin-2-one To a solution of (4S,5S)-4-(((tert-butyldiphenylsilyl)oxy) methyl)-5-(4-methoxyphenyl)-oxazolidin-2-one (1.65 g, 3.57 mmol), 4-(4,6-dichloropyrimidin-2-yl)morpholine (920 mg, 3.93 mmol) and Cs₂CO₃ (1.75 g, 5.36 mmol) in dioxane (20 mL) was added after purging with argon 4,5-bis(diphenylphosphino)-9,9-dimethylxanthene (145 mg, 250 μmol) and Pd₂(dba)₃ (65 mg, 0.071 mmol), and the reaction mixture was heated for 5 h at 100° C. The reaction mixture was added to 10% aqueous NaHCO₃ solution and extracted with EtOAc. Combined extracts were washed with brine, dried over MgSO₄, filtered and concentrated. The residue was purified by column chromatography using EtOAc in heptane from 0% to 50% in order to give the title compound as a white solid (2.33 g, 94%). TLC (heptane/EtOAc 1:1) R_f=0.52; LC-MS: [M+H] 659,661; Rt 1.58 min; (LCMS method 2). ¹H NMR (400 MHz, CDCl₃): 7.64 (m, 4H), 7.54 (s, 1H), 7.55-7.35 (m, 6H), 7.26 (m, 2H), 6.95 (d, 2H), 5.21 (d, 1H), 4.56 (m, 1H), 4.22 (dd, 1H), 3.96 (dd, 1H), 3.84 (s, 3H), 3.60-3.40 (m, 8H), 1.09 (s, 9H).

b) (4S,5S)-3-(2'-Amino-2-morpholino-4'-(trifluoromethyl)-[4,5'-bipyrimidin]-6-yl)-4-(((tert-butyldiphenylsilyl)oxy)methyl)-5-(4-methoxyphenyl) oxazolidin-2-one A solution of (4S,5S)-4-(((tert-butyldiphenylsilyl)oxy) methyl)-3-(6-chloro-2-morpholinopyrimidin-4-yl)-5-(4-methoxyphenyl)oxazolidin-2-one (150 mg, 228 μmol), 5-(4, 4,5,5-tetramethyl-1,3,2-dioxaborolan-2-yl)-4-(trifluoromethyl)pyrimidin-2-amine (108 mg, 364 μmol), 20% aqueous Na₂CO₃ (0.24 mL, 2.28 mmol), and PdCl₂ (dppf)-CH₂Cl₂ (18.6 mg, 23 μmol) in DME (2 mL) under argon was stirred at 80° C. for 8 h. The reaction mixture was diluted with EtOAc and washed with saturated NaHCO₃ solution, H₂O and brine, dried over MgSO₄, filtered and concentrated. The residue was purified by column chromatography using EtOAc in heptane from 0% to 33% in order to give the title compound as a light yellow foam (68 mg, 28%): TLC c) (4S,5S)-3-(2'-Amino-2-morpholino-4'-(trifluoromethyl)-[4,5'-bipyrimidin]-6-yl)-4-(hydroxymethyl)-5-(4-methoxyphenyl)oxazolidin-2-one To a solution of (4S,5S)-3-(2'-amino-2-morpholino-4'-(trifluoromethyl)-[4,5'-bipyrimidin]-6-yl)-4-(((tert-butyldiphenylsilyl)oxy)methyl)-5-(4-methoxyphenyl)oxazolidin-2-one (68 mg, 65 μmol) in THF (2 mL) was added dopwise at 0° C. 1M TBAF in THF (0.05 ml, 0.05 mmol), and the resulting mixture was stirred for 30 min at 0° C. and 1 h at RT. The reaction mixture was concentrated, and the residue was purified by column chromatography using a ratio of hexane/CH$_2$Cl$_2$/MeOH from 100:100:5 to 0:100:5, followed by preparative HPLC (Waters Sun Fire C18, 30×100 mm, 5 um; 0.1% TFA-water/acetonitrile; gradient acetonitrile 30-50% in 20 min) to afford the title compound as white solid (18 mg, 50%); TLC (CH$_2$Cl$_2$/MeOH 19:1) R$_f$=0.40; t$_R$=0.998 min (UPLC 1); LC-MS: [M+H] 548; Rt 0.96 min; (LCMS method 2). $^1$H NMR (600 MHz, DMSO-d$_6$): 8.60 (s, 1H), 7.64 (br s, 2H), 7.53 (s, 1H), 7.34 (d, 2H), 7.00 (d, 2H), 5.58 (d, 1H), 5.32 (t, 1H), 4.59 (m, 1H), 4.00 (m, 1H), 3.82 (m, 1H), 3.76 (s, 3H), 3.75-3.55 (m, 81-1).

Examples 4 to 14

Examples 4 to 14 in Table 1 below can be made using procedures analogous to those described in examples 1-3, using the appropriate boronic ester intermediate and oxazolidinone.

TABLE 1

| Example Number | Structure and Name | $^1$H NMR | LC/MS |
|---|---|---|---|
| 4 | 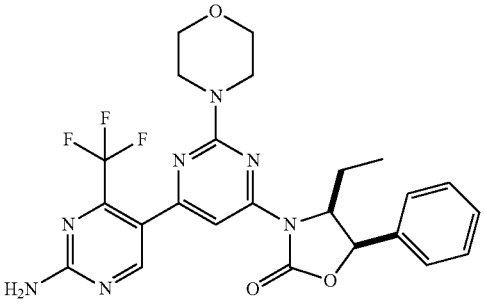<br>(4S*,5R*)-3-(2'-Amino-2-morpholin-4'-(trifluoromethyl)-[4,5'-bipyrimidin]-6-yl)-4-ethyl-5-phenyloxazolidin-2-one | $^1$H NMR (400 MHz, CHCl$_3$-d): 8.64 (s, 1H), 7.69 (s, 1H), 7.39-7.50 (m, 5H), 5.82 (d, 1H), 5.46 (br s, 2H), 5.02-4.96 (m, 1H), 3.87-3.73 (m, 8H), 1.84-1.72 (m, 1H), 1.59-1.66 (m, 1H), 0.52 (t, 3H). | LCMS (method 2): Retention Time: 1.19 min Mass [M + H]: 516.2 |
| 5 | 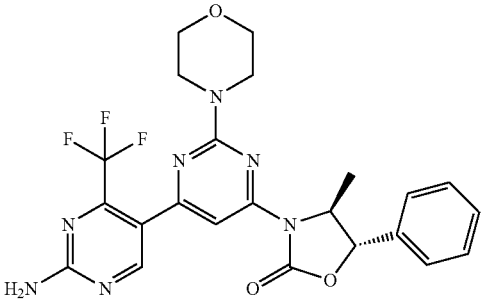<br>(4S,5S)-3-(2'-Amino-2-morpholino-4'-(trifluoromethyl)-[4,5'-bipyrimidin]-6-yl)-4-methyl-5-phenyloxazolidin-2-one | $^1$H NMR (600 MHz, DMSO-d$_6$): 8.61 (s, 1H), 7.64 (br s, 2H), 7.51-7.35 (m, 6H), 5.45 (d, 1H), 4.73-4.52 (m, 1H), 3.78-3.54 (m, 8H), 1.61 (d, 3H). | LCMS (method 2): Retention Time: 1.11 min Mass (ES+): 502.2 |

TABLE 1-continued

| Example Number | Structure and Name | $^1$H NMR | LC/MS |
|---|---|---|---|
| 6 | 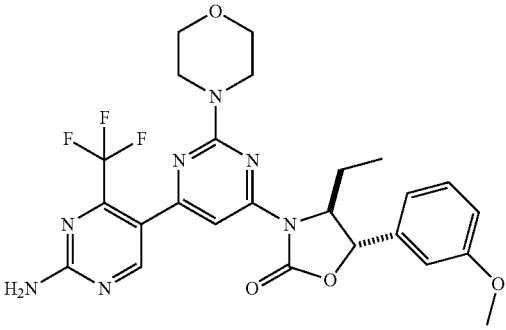<br>(4R*,5R*)-3-(2'-Amino-2-morpholino-4'-(trifluoromethyl)-[4,5'-bipyrimidin]-6-yl)-4-ethyl-5-(3-methoxyphenyl)oxazolidin-2-one | $^1$H NMR (400 MHz, CHCl$_3$-d): 8.62 (s, 1H), 7.67 (s, 1H), 7.32-7.40 (t, 1H), 7.01-6.86 (m, 3H), 5.50 (br s, 2H), 5.29 (d, 1H), 4.60-4.64 (m, 1H), 3.85 (s, 3H), 3.76 (m, 8H), 2.30-2.00 (m, 2H), 1.11 (t, 3H). | LCMS (method 2): Retention Time: 1.18 min<br>Mass [M + H]: 546.2 |
| 7 | 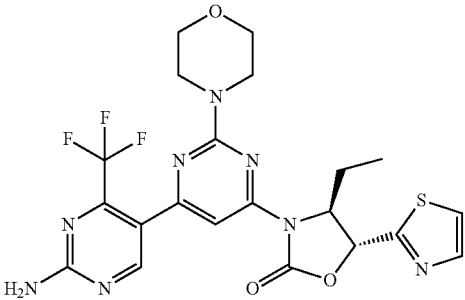<br>(4S,5R)-3-(2'-Amino-2-morpholino-4'-(trifluoromethyl)-[4,5'-bipyrimidin]-6-yl)-4-ethyl-5-(thiazol-2-yl)oxazolidin-2-one | | LCMS (method 1): Retention Time: 1.06 min<br>Mass [M + H]: 523.1 |
| 8 | 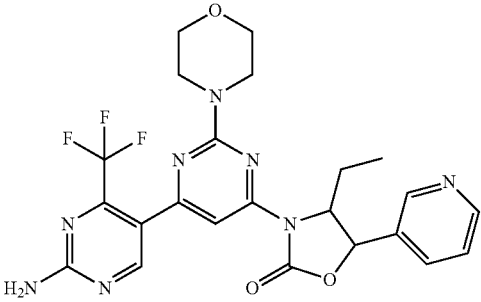<br>3-(2'-Amino-2-morpholin-4-yl-4'-trifluoromethyl-[4,5']bipyrimidinyl-6-yl)-4-ethyl-5-pyridin-3-yl-oxazolidin-2-one | | LCMS (method 1): Retention Time: 0.96 min<br>Mass [M + H]: 517.5 |

TABLE 1-continued

| Example Number | Structure and Name | ¹H NMR | LC/MS |
|---|---|---|---|
| 9 | 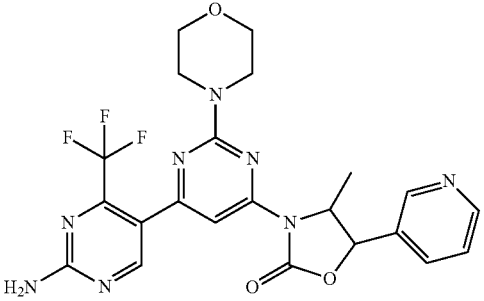<br>3-(2'-Amino-2-morpholin-4-yl-4'-trifluoromethyl-[4,5']bipyrimidinyl-6-yl)-4-methyl-5-pyridin-3-yl-oxazolidin-2-one | Mixture of cis and trans diastereoisomers in a ratio of 2 to 1:<br>cis diastereoisomer:<br>¹H NMR (400 MHz, DMSO-d$_6$): 8.78-8.58 (m, 3H), 7.96-7.88 (m, 1H), 7.62 (br s, 2H), 7.54-7.48 (m, 2H), 6.05 (d, 1H), 5.27-5.20 (m, 1H), 3.78-3.62 (m, 8H), 0.95 (d, 3H)<br>trans diastereoisomer:<br>¹H NMR (400 MHz, DMSO-d$_6$): 8.78-8.58 (m, 3H), 7.96-7.88 (m, 1H), 7.62 (br s, 2H), 7.54-7.48 (m, 1H), 7.45 (s, 1H), 5.53 (d, 1H), 4.77-4.70 (m, 1H), 3.78-3.62 (m, 8H), 1.62 (d, 3H) | LCMS (method 1): Retention Time: 0.91 min<br>Mass [M + H]: 503.2 |
| 10 | 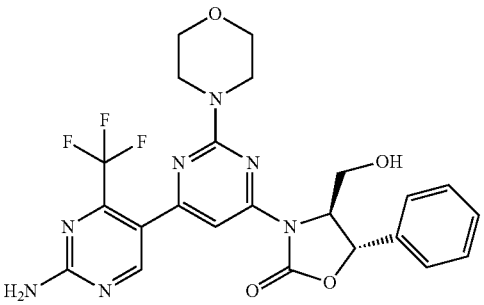<br>(4S,5S)-3-(2'-Amino-2-morpholin-4-yl-4'-trifluoromethyl-[4,5']bipyrimidinyl-6-yl)-4-hydroxymethyl-5-phenyl-oxazolidin-2-one | ¹H NMR (400 MHz, DMSO-d$_6$): 8.61 (s, 1H), 7.61 (br s, 2H), 7.53 (s, 1H), 7.50-7.31 (m, 5H), 5.65 (d, 1H), 5.34 (t, 1H), 4.66-4.59 (m, 1H), 4.08-3.96 (m, 1H), 3.92-3.83 (m, 1H), 3.73-3.57 (m, 8H). | LCMS (method 2): Retention Time: 0.97 min<br>Mass [M + H]: 518.1 |
| 11 | 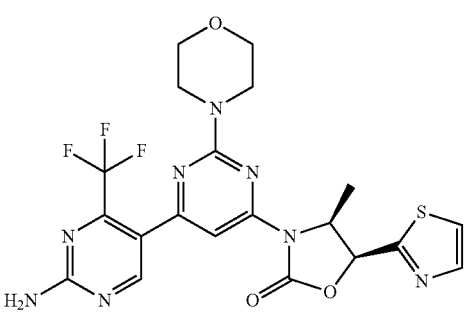<br>(4S,5S)-3-(2'-Amino-2-morpholin-4-yl-4'-trifluoromethyl-[4,5']bipyrimidinyl-6-yl)-4-methyl-5-thiazol-2-yl-oxazolidin-2-one | ¹H NMR (400 MHz, DMSO-d): 8.60 (s, 1H), 7.98 (d, 1H), 7.89 (d, 1H), 7.64 (br s, 2H), 7.44 (s, 1H), 6.28 (d, 1H), 5.30-5.20 (m, 1H), 3.78-3.61 (m, 8H), 1.05 (d, 3H). | LCMS (method 1): Retention Time: 1.01 min<br>Mass [M + H]: 509.2 |

TABLE 1-continued

| Example Number | Structure and Name | ¹H NMR | LC/MS |
|---|---|---|---|
| 12 | 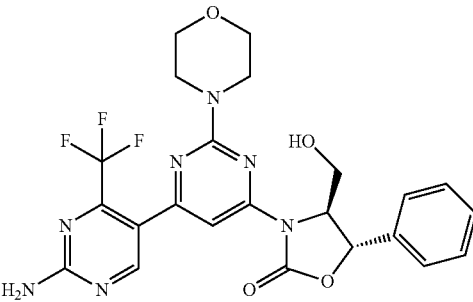<br>(4S,5S)-3-(2'-Amino-2-morpholino-4'-(trifluoromethyl)-[4,5'-bipyrimidin]-6-yl)-4-(hydroxymethyl)-5-(4-(2-methoxyethoxy)phenyl)oxazolidin-2-one | ¹H NMR (600 MHz, DMSO-$d_6$): 8.53 (s, 1H), 7.64 (br, s, 2H), 7.53 (s, 1H), 7.32 (d, 2H), 7.00 (d, 2H), 5.58 (d, 1H), 5.32 (t, 1H), 4.60 (m, 1H), 4.09 (m, 2H), 3.99 (m, 1H), 3.82 (m, 1H), 3.55-3.75 (m, 10H); 3.34 (s, 3H). | LCMS (method 2): Retention Time: 0.93 min Mass [M + H]: 592.1 |
| 13 | 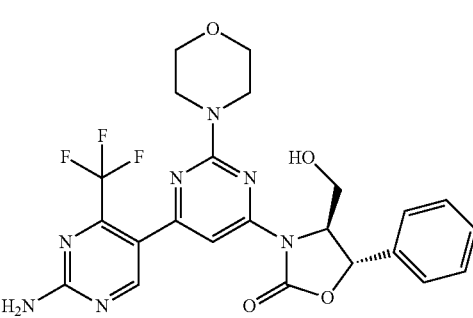<br>(4S,5S)-3-(2'-Amino-2-morpholino-4'-(trifluoromethyl)-[4,5'-bipyrimidin]-6-yl)-5-(4-(2-hydroxyethoxy)phenyl)-4-(hydroxymethyl)oxazolidin-2-one | ¹H NMR (400 MHz, DMSO-$d_6$): 8.61 (s, 1H), 7.63 (br s, 2H), 7.54 (s, 1H), 7.33 (d, 2H), 7.02 (d, 2H), 5.58 (d, 1H), 5.31 (t, 1H), 4.87 (t, 1H), 4.61 (m, 1H), 4.10-3.90 (m, 3H), 3.82 (m, 1H), 3.75-3.55 (m, 10H). | LCMS (method 1): Retention Time: 0.79 min Mass [M + H]: 578.2 |
| 14 | 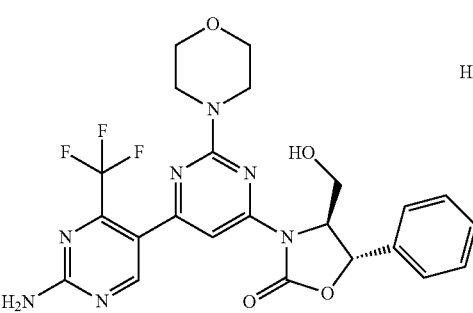<br>(4S,5S)-3-(2'-Amino-2-morpholino-4'-(trifluoromethyl)-[4,5'-bipyrimidin]-6-yl)-4-(hydroxymethyl)-5-(4-(3-hydroxypropoxy)phenyl)oxazolidin-2-one | ¹H NMR (400 MHz, DMSO-$d_6$): 8.60 (s, 1H), 7.62 (br s, 2H), 7.53 (s, 1H), 7.31 (d, 2H), 7.00 (d, 2H), 5.57 (d, 1H), 5.30 (t, 1H), 4.60 (m, 1H), 4.53 (t, 1H), 4.04 (m, 2H), 3.99 (m, 1H), 3.81(m, 1H), 3.63 (m, 8H), 3.55 (m, 2H), 1.85 (m, 2H). | LCMS (method 1): Retention Time: 0.84 min Mass [M + H]: 592.3 |

Biological Activity

The activity of a compound according to the present invention can be assessed by the following in vitro & in vivo methods Preparation of Compound Dilutions (384-Well)

Test compounds were dissolved in DMSO (10 mM) and transferred into 1.4 mL flat bottom or V-shaped Matrix tubes carrying a unique 2D matrix chip by individual Novartis compound hubs. The numbers of these chips were distinctively linked to Novartis Pharma Numbers. The stock solutions were stored at −20° C. if not used immediately. For the test procedure the vials were defrosted and identified by a scanner whereby a working sheet was generated that guided the subsequent working steps.

Compounds were either manually diluted in DMSO for individual experiments (96 wells enabling 10 cpds at 8 (single points) concentrations) as described in or prepared as described below if tested for profiling in 384-wells. This format enabled the assay of maximally 40 individual test compounds at 8 concentrations (single points) including 4 reference compounds. The dilution protocol included the production of "pre-dilution plates", "master plates" and "assay plates".

Pre-Dilution Plates: 96 polypropylene well plates were used as pre-dilution plates. A total of 4 pre-dilution plates were prepared including 10 test compounds each on the plate positions A1-A10, one standard compound at A11 and one DMSO control at A12. The pattern of the dilution steps is summarized in Table 1. Programs have been written to run these pipetting steps on the HamiltonSTAR robots.

TABLE 1

Dilution pattern for pre-dilution plates

| c | Vol ($\mu$L) | Conc. ($\mu$M) |   | Vol ($\mu$L) DMSO |   | Vol ($\mu$L) | Conc ($\mu$M) | Dil. ratio | Final concentration ($\mu$M) |
|---|---|---|---|---|---|---|---|---|---|
| A | 30 | 10'000 | + | 135 | → | 165 | 1'820 | 1:5.5 | 10 |
| B | 50 | 1'820 | + | 116 | → | 166 | 546 | 1:3.33 | 3 |
| C | 50 | 546 | + | 100 | → | 150 | 182 | 1:3 | 1 |
| D | 50 | 182 | + | 116 | → | 166 | 54.6 | 1:3.33 | 0.3 |
| E | 50 | 54.6 | + | 100 | → | 150 | 18.2 | 1:3 | 0.1 |
| F | 50 | 18.2 | + | 116 | → | 166 | 5.46 | 1:3.33 | 0.03 |
| G | 50 | 5.46 | + | 100 | → | 150 | 1.82 | 1:3 | 0.01 |
| H | 50 | 1.82 | + | 116 | → | 166 | 0.546 | 1:3.33 | 0.003 |

DMSO was saturated with $H_2O$ to a concentration of 10%.
Vol: Volume,
Conc: Concentration,
Dil. ratio: Dilution ratio,
Fin. c: Final concentration.

Master Plates: 100 $\mu$L of individual compound dilutions including standard compound and controls of the 4 "pre-dilution plates" were transferred into a 384 "master plate" including the following concentrations 1'820, 564, 182, 54.6, 18.2, 5.46, 1.82 and 0.546 $\mu$M, respectively in 90% DMSO.

Assay Plates: Identical "assay plates" were then prepared by pipetting 50 nL each of compound dilutions of the "master plates" into 384-well "assay plates". The compounds were mixed with 4.5 $\mu$L of assays components plus 4.5 $\mu$L enzyme corresponding to a 1:181 dilution enabling the final concentration of 10, 3.0, 1.0, 0.3, 0.1, 0.03, 0.01 and 0.003 $\mu$M, respectively. The preparation of the "master plates" was handled by the Matrix PlateMate Plus robot and replication of "assay plates" by the HummingBird robot.

Method to Generate Expression Constructs

Catalytically active human PI3K$\alpha$, PI3K$\beta$, PI3K$\delta$, and mTOR were cloned, expressed and purified as described (Maira S M, Stauffer F, Brueggen J, Furet P, Schnell C, Fritsch C, Brachmann S, Chène P, de Pover A, Schoemaker K, Fabbro D, Gabriel D, Simonen M, Murphy L, Finan P, Sellers W, García-Echeverría C (2008), *Mol Cancer Ther.* 7:1851-63 and Maira S M, Pecchi S, Brueggen J, Huh K, Schnell C, Fritsch C, Nagel T, Wiesmann M, Brachmann S, Dorsch M, Chène P, Schoemaker K, De Pover A, Menezes D, Fabbro D, Sellers W, García-Echeverría C, Voliva C F (2011), *Mol. Cancer Ther.* accepted).

Biochemical Assays for PI3Kalpha, PI3Kbeta

The luminescence-based ATP detection reagent KinaseGlo was obtained from Promega, (Cat. No. V6714, Lot No. 236161) through Catalys, Wallisellen, Switzerland. (L-alpha-phosphatidylinositol (PI), Liver, Bovine) were obtained from Avanti Polar Lipid (Cat. No. 840042C, Lot#LPI-274), Phosphatidylinositol-4,5-bisphosphate (PIP(4,5)2 (Avanti, Cat. No. 840046X) or L-$\alpha$-phosphatidylinositol (PI) was obtained from Avanti Polar Lipid (Cat. No. 840042C, Lot#LPI-274).

L-$\alpha$-Phosphatidylserine (PS) was from Avanti Polar Lipid (Cat. No. 840032C), n-Octylglucoside Avanti Polar Lipid (Cat. No. 10634425001). Luminescence is a well established readout to determine ATP concentrations and can thus be used to follow the activity of many kinases regardless of their substrate. The Kinase Glo Luminescent Kinase Assay (Promega, Madison/Wis., USA) is a homogeneous HTS method of measuring kinase activity by quantifying the amount of ATP remaining in solution following a kinase reaction.

50 nL of compound dilutions were dispensed onto black 384-well low volume Non Binding Styrene (NBS) plates (Costar Cat. No. NBS#3676) as described in section 8.2. L-$\alpha$-phosphatidylinositol (PI), provided as 10 mg/ml solution in methanol, was transferred into a glass tube and dried under nitrogen beam. It was then resuspended in 3% OctylGlucoside by vortexing and stored at 4° C. 5 $\mu$L of a mix of PI/OG with the PI3Ka and Pi3Kb subtypes were added. Kinase reactions were started by addition of 5 $\mu$l of ATP-mix containing in a final volume 10 $\mu$L 10 mM TRIS-HCl pH 7.5, 3 mM $MgCl_2$, 50 mM NaCl, 0.05% CHAPS, 1 mM DTT and 1 $\mu$M ATP, and occurred at room temperature. Reactions were stopped with 10 $\mu$l of KinaseGlo and plates were read 10 mins later in a Synergy2 reader using an integration time of 0.1 seconds per well. 2.5 $\mu$M of NVP-BGT226 (standard) was added to the assay plates to generate the 100% inhibition of the kinase reaction, and the 0% inhibition was given by the solvent vehicle (90% DMSO in water). NVP-BGT226 was used as a reference compound and included in all assay plates in the form of 16 dilution points in duplicate.

$IC_{50}$ values of the percentage inhibition of each compound at 8 concentrations (usually 10, 3.0, 1.0, 0.3, 0.1, 0.030, 0.010 and 0.003 $\mu$M) n=2 were derived by fitting a sigmoidal dose-response curve to a plot of assay readout over inhibitor concentration as described. All fits were performed with the program XLfit4 (ID Business Solutions, Guildford, UK).

Biochemical Assays for PI3Kdelta, PI3Kgamma

The TR-FRET Adapta™ Universal Kinase Assay Kit was purchased from Invitrogen Corporation (Carlsbad/CA, USA) (Cat. No. PV5099). The kit contains the following reagents: Adapta Eu-anti-ADP Antibody (Europium labeled anti-ADP antibody in HEPES buffered saline, Cat. No. PV5097), Alexa Fluor® 647-labeled ADP tracer (Alexa Fluor® 647-labeled ADP tracer in HEPES buffered saline, Cat. No. PV5098), proprietary TR-FRET dilution buffer pH 7.5 (Cat. No. PV3574).

PIK3CD substrate Phosphatidylinositol was obtained from Invitrogen (vesicules consisting of 2 mM PI in 50 mM HEPES pH7.5; Cat. No. PV5371). PIK3CG substrate Phosphatidylinositol-4,5-bisphosphate (PIP(4,5)2 was obtained from Invitrogen (PIP2:PS large unilamellar vesicules consisting of 1 mM PIP2: 19 mM PS in 50 mM HEPES pH7.5, 3 mM MgCl2, 1 mM EGTA; Cat. No. PV5100).

Time-Resolved Fluorescence Resonance Energy Transfer (TR-FRET) is a technology based on energy transfer between two adjacent dyes, from an excited electron in one dye (the donor) to an electron of an adjacent dye (the acceptor) through resonance, then released as a photon. This energy transfer is detected by an increase in the fluorescence emission of the acceptor, and a decrease in the fluorescence emission of the donor. TR-FRET assays for protein kinases use a long-lifetime lanthanide Terbium or Europium chelates as the donor species which overcome interference from compound autofluorescence or light scatter from precipitated compounds, by introducing a delay after excitation by a flashlamp excitation source. Results are often expressed as a ratio of the intensities of the acceptor and donor fluorophores. The ratiometric nature of such a value corrects for differences in assay volumes between wells, as well as corrects for quenching effects due to colored compounds. The Adapta™ assay can be divided into two phases: a kinase reaction phase and an ADP detection phase. In the kinase reaction phase, all kinase reaction components are added to the well and the reaction is allowed to incubate for a set period of time specific for each kinase. After the reaction, a detection solution of Eu-labeled anti-ADP antibody, Alexa Fluor® 647-labeled ADP tracer, and EDTA (to stop the kinase reaction) are added to the assay well. ADP formed by the kinase reaction will displace the Alexa Fluor® 647-labeled ADP tracer from the antibody, resulting in a decrease in TR-FRET signal. In the presence of an inhibitor, the amount of ADP formed by the kinase reaction is reduced, and the resulting intact antibody-tracer interaction maintains a high TR-FRET signal. In the Adapta™ assay, the donor (Europium-anti-ADP antibody) is excited at 340 nm and will transfer its energy to the acceptor (Alexa Fluor® 647-labeled ADP tracer). The emission from the Alexa Fluor® 647 can be monitored with a filter centered at 665 nm because it is located between the emission peaks of the donor, which is measured at 615/620 nm.

50 nL of compound dilutions were dispensed onto white 384-well small volume polystyrene plate as described in section 2.2. Then 5 µL of PI3Kg and PI3Kd and lipid substrate (PI or PIP2:PS) followed by 5 µL of ATP (final assay volume 10 µL) are incubated at RT. The standard reaction buffer for the Adapta™ TR-FRET assay contained 10 mM Tris-HCl pH 7.5, 3 mM MgCl2, 50 mM NaCl, 1 mM DTT, 0.05% CHAPS. Reactions were stopped with 5 µL of a mixture of EDTA containing the Eu-labeled anti-ADP antibody and the Alexa Fluor® 647-labeled ADP tracer in TR-FRET dilution buffer (proprietary to IVG). Plates are read 15 to 60 mins later in a Synergy2 reader using an integration time of 0.4 seconds and a delay of 0.05 seconds. Control for the 100% inhibition of the kinase reaction was performed by replacing the PI3K by the standard reaction buffer. The control for the 0% inhibition was given by the solvent vehicle of the compounds (90% DMSO in $H_2O$). The standard compound NVP-BGT226 was used as a reference compound and included in all assay plates in the form of 16 dilution points in duplicate.

Data are analyzed using Excel fit software or Graphpad Prism. $EC_{50}$ values were derived by fitting a sigmoidal dose-response curve to a plot of assay readout over inhibitor concentration. All fits were performed with the program XLfit4 (ID Business Solutions, Guildford, UK). Determination of $EC_{50}$ values of the percentage inhibition of each compound at 8 concentrations (usually 10, 3.0, 1.0, 0.3, 0.1, 0.030, 0.010 and 0.003 µM) n=2 were derived by fitting a sigmoidal dose-response curve to a plot of assay readout over inhibitor concentration. All fits were performed with the program XLfit4 (ID Business Solutions, Guildford, UK).

Biochemical Assay for mTOR

TR-FRET assays for protein kinases uses a long-lifetime lanthanide Terbium or Europium chelates as the donor species which overcome interference by compound autofluorescence or light scatter from precipitated compounds, by introducing a delay after excitation by a flashlamp excitation source. Results are often expressed as a ratio of the intensities of the acceptor and donor fluorophores. The ratiometric nature of such a value corrects for differences in assay volumes between wells, as well as corrects for quenching effects due to colored compounds.

Binding Assays are based on the binding and displacement of an Alexa Fluor® 647-labeled, ATP-competitive kinase inhibitors to the kinase of interest. Invitrogen's "Kinase Tracers" have been developed to address a wide range of kinase targets and are based on ATP-competitive kinase inhibitors, making them suitable for detection of any compounds that bind to the ATP site or to an allosteric site altering the conformation of the ATP site. Inhibitors that bind the ATP site include both Type I kinase inhibitors, which bind solely to the ATP site, and Type II inhibitors (e.g., Gleevec®/Imatinib, Sorafenib, BIRB-796), which bind to both the ATP site and a hydrophobic site exposed in the DFG-out (non-active) conformation. Type III inhibitors are compounds that do not compete with ATP are loosely referred to as allosteric inhibitors. A study of 15 diverse Type III inhibitors demonstrated that all but one compound was detected in the binding assay with equivalent potency to activity assays. The sole exception was a substrate-competitive compound, and thus not a true allosteric inhibitor.

In contrast to most fluorescence-based kinase activity assays, LanthaScreen® $Eu^{3+}$ Kinase Binding Assays can be read continuously, which facilitates evaluation of compounds with slow binding kinetics. Also, unlike most activity assays, binding assays can be performed using either active or non-activated kinase preparations, which enables characterization of compounds that bind preferentially to non-activated kinases, such as Gleevec®/imatinib and some allosteric inhibitors.

In the Lanthascreen™ kinase binding assay, the donor ($Eu^{3+}$-anti-GST antibody) is excited at 340 nm and will transfer its energy to the acceptor (Alexa Fluor® 647-labeled ATP-competitive kinase inhibitor=Tracer-314). The emission from the Tracer-314 (Alexa Fluor® 647 inhibitor) can be monitored with a filter centered at 665 nm because it is located between the emission peaks of the donor, which is measured at 615/620 nm. The binding of both, the Tracer-314 and $Eu^{3+}$-anti-GST antibody, to the kinase results in a high degree of FRET from the $Eu^{3+}$-donor fluorophore to the Alexa-Fluor® 647-acceptor fluorophore on the Tracer-314. Binding of an inhibitor to the kinase competes for binding with the tracer, resulting in a loss of FRET.

50 nL of compound dilutions were dispensed onto white 384-well small volume polystyrene plate as described in section 2.2. Then 5 µL of GST-mTOR and Europium-anti-GST antibody followed by 5 µL of tracer-314 (final assay volume 10 µL) are incubated at RT. The standard reaction buffer for the Lanthascreen™ kinase binding assay contained 50 mM HEPES pH 7.5, 5 mM MgCl2, 1 mM EGTA, 0.01% Pluronic F-127. Plates are read 60 mins later in a Synergy2 reader using an integration time of 0.2 microseconds and a delay of 0.1 microseconds.

To calculate the emission ratio, the signal emitted at 665 nm from the acceptor (Alexa Fluor® 647-labeled Tracer-314) is divided by the signal emitted at 620 nm from the donor ($Eu^{3+}$ anti-GST antibody)

Control for the 0% inhibition was given by the solvent vehicle of the compounds (90% DMSO in $H_2O$). Control for the relative 100% inhibition was performed by adding 10 µM in the mix containing GST-mTOR and Europium anti-GST antibody. An additional control for the absolute 0% inhibition is given by $Eu^{3+}$ anti-GST antibody without GST-mTOR.

Cellular Assays for PI3Kalpha, Beta and Delta

AlphaScreen (Amplified Luminescent Proximity Homogeneous Assay, ALPHA, Perkin Elmer) is a non-radioactive bead-based proximity assay technology to study biomolecular interactions in a homogenous microliter plate format. The brand name SureFire denotes AlphaScreen assays that are adapted to quantify the phosphorylation of endogenous cellular proteins in cell lysates, by using matched antibody pairs, which consist of an anti-phospho-kinase and an anti-kinase antibody. The assay allows characterization of kinase signaling in cells as well as measurement of kinase inhibitor effects. The AlphaScreen technology provides several advantages over standard assay techniques such as ELISA, as it avoids time-consuming washing procedures and reduces plate handling. Furthermore, it is miniaturizable at least to a 384-well format and provides sensitivity down to the femtomolar range, dependent on the affinity of the antibodies included in the individual AlphaScreen SureFire assay kit. High sensitivity is reached by an intrinsic amplification mechanism, which involves production of singlet oxygen molecules. SureFire assay kits are commercially available for specific targets and include pairs of validated antibodies (PerkinElmer). This report describes common procedures applied for AlphaScreen SureFire assays and respective semi-automated steps for routine kinase inhibitor profiling in cell-based assays.

The Rat-1 cell lines stably overexpressing activated PI3K class I isoforms Rat-1 pBABEpuro Myr-HA-hp110 delta (Rat-1_PI3Kdelta) and Rat-1 pBABEpuro Myr-HA-hp110alpha (Rat-1_PI3Kalpha) and Rat-1 pBABEpuro Myr-HA-hp110 beta (Rat-1_PI3beta) were prepared as described (Maira S M, Stauffer F, Brueggen J, Furet P, Schnell C, Fritsch C, Brachmann S, Chène P, de Pover A, Schoemaker K, Fabbro D, Gabriel D, Simonen M, Murphy L, Finan P, Sellers W, García-Echeverría C (2008), Mol Cancer Ther. 7:1851-63 and Maira S M, Pecchi S, Brueggen J, Huh K, Schnell C, Fritsch C, Nagel T, Wiesmann M, Brachmann S, Dorsch M, Chène P, Schoemaker K, De Pover A, Menezes D, Fabbro D, Sellers W, García-Echeverría C, Voliva C F (2011), *Mol. Cancer Ther*, accepted). All cell lines were cultivated in complete growth medium (DMEM high glucose, 10% (v/v) fetal bovine serum, 1% (v/v) MEM NEAA, 10 mM HEPES, 2 mM L-glutamine, puromycin (10 µg/mL for Rat-1_PI3Kdelta and Rat-1_PI3Kalpha, 4 ug/mL for Rat-1_PI3beta), 1% (v/v) Pen/Strep) to 90% confluency at 37° C./5% $CO_2$/90% humidity in a humidified $CO_2$ incubator and were split twice a week.

The following materials were used for p-AKT(S473) detection in Rat-1 cell lysates: Dulbecco's modified Eagle's medium (DMEM) high glucose (Gibco Invitrogen, Basel, Switzerland, Cat. No. 41965), Heat Inactivated Fetal Bovine Serum, Qualified (HI FBS; Gibco Invitrogen, Basel, Switzerland, Lot. No. 16140), MEM non essential amino acids (NEAA; Gibco Invitrogen, Basel, Switzerland, Cat. No. 11140), HEPES (Gibco Invitrogen, Basel, Switzerland, Cat. No. 15630), Penicillin/Streptomycin (Pen/Strep, 100x; Gibco Invitrogen, Basel, Switzerland, Cat. No. 15140-122), L-Glutamine (Gibco Invitrogen, Basel, Switzerland, Cat. No. 25030), Puromycin (Sigma Aldrich, Buchs, Switzerland, Cat. No. P9620), DMSO (MERCK, Dietikon, Switzerland, Cat. No. 8.02912.2500), $H_2O$, MilliQ-$H_2O$ unless otherwise stated (MILLIPORE QGARDOOR1, Millipore, Zug, Switzerland), Bovine serum albumine (BSA; Sigma Aldrich, Buchs, Switzerland Cat. No. A8412), SureFire p-Akt 1/2 (Ser473) Assay Kit (PerkinElmer, Schwerzenbach, Switzerland, Cat. No. TGRAS50K).

The p-Akt(S473) SureFire assay measures the phosphorylation of endogenous cellular Akt 1/2 at Ser473 in cell lysates. Using Rat-1 cells stably expressing myr-HA-tagged versions of the human PI3Kdelta, PI3Kalpha, or PI3Kbeta p110 catalytic subunit isoforms, the assay was developed as a two-plate protocol in a 384-well format. For compound testing, the cells were seeded at a density of 4000 (Rat-1_PI3Kdelta), 7500 (Rat-1_PI3Kalpha), or 6200 (Rat-1_PI3Kbeta) cells in 20 ul complete growth medium into cell culture treated 384-well plates and were grown at 37° C./5% $CO_2$/90 humidity for 24 h. Shortly before compound transfer, the complete medium was removed, 30 ul assay buffer (DMEM high glucose, 1×MEM NEAA, 10 mM HEPES, 2 mM L-glutamine, 0.1% (w/v) BSA) was added and 10 ul of the compound predilutions were transferred to the cells. For testing after February 2010, assay buffer was substituted for complete growth medium, which revealed similar results (data not shown). After treatment with compound for 1 h, the cells were lysed by the addition of 20 ul lysis buffer supplemented with 0.24% (w/v) BSA. Detection of p-AKT(Ser473) was performed with the SureFire p-Akt 1/2 (Ser473) Assay Kit according to the manufacturer's instructions using 5 ul of cell lysate in a total detection volume of 12 ul.

$IC_{50}$ values of the percentage inhibition of each compound at 8 concentrations (usually 10, 3.0, 1.0, 0.3, 0.1, 0.030, 0.010 and 0.003 µM) n=2 were derived by fitting a sigmoidal dose-response curve to a plot of assay readout over inhibitor concentration as described. All fits were performed with the program XLfit4 (ID Business Solutions, Guildford, UK).

Cellular Assay for mTOR

A cell based assay (384-well format) was developed for determination of compound effects on cellular mTOR activity in MEF (mouse embryo fibroblasts) cells derived from mice lacking TSC1 (Tuberosclerosis Complex1) a potent suppressor of mTOR activity. Due to lack of TSC1, mTOR is constitutively activated resulting in permanent phosphorylation of Thr 389 of S6 kinase 1 (S6K1) which is one of the downstream targets of mTOR.

Using a SureFire Kit that enables to determine the phosphorylation of Thr389 on the S6K1 an assay was developed, validated and implemented in the Alpha-Screen format that allows the quantitative determination of phospho-T389 of S6K1 in cell lysates. Treatment of the MEF TSC1−/− cells with mTOR specific (or mTOR pathway-) inhibitors dose-dependently reduced the levels of phospho-T389 on S6K1 allowing calculation of IC50 values. These were in agreement with those values obtained with the biochemical mTOR ATP-binding assay enabling a quantitative comparison of potency of mTOR inhibitors.

TSC1−/− MEFs cells (Kwiatkowski, D. J., Zhang, H., Bandura, J. L., Heiberger, K. M., Glogauer, M., el-Hashemite, N., and Onda, H. (2002) *Hum. Mal. Genet*. 11, 525-534) were cultured in DMEM high glucose medium supplemented with 10% FBS (Invitrogen), 2 mM Glutamine and 1% (wlv) Penicillin/Streptomycin at 37° C., 5% $CO_2$.

The SureFire kit for determination of P70S6kinase phosphorylation was purchased from Perkin Elmer (p70S6K p-T389, #TGR70S50K) and the assay was performed according to the instructions of the supplier and according to the generic method for SureFire assays. Shortly, 5 μL cell lysate per well were transferred to 384-well white proxy-plates (for luminescent readout) and mixed with 7 μL A and 5 μL B (final volume: 12 μL). After 3 h incubation in the dark at RT luminescence was read with the Envision Reader (Perkin Elmer). Untreated cells were used as control (high control) and cells treated with 3 μM BEZ235 were used as low control. The assay window between the signals obtained for the high and the low controls were defined as 100% and compound effects were expressed as percent inhibition. IC50 values were calculated from the dose response curves by graphical extrapolation.

The results obtained using the above-described assays are provided in the following tables.

| Biochemical PI3Kalpha | |
|---|---|
| Example no. | PI3Ka/IC50 [umol I-1] |
| 1 | 0.006 |
| 2 | 0.078 |
| 3 | 0.005 |
| 4 | 0.047 |
| 5 | 0.023 |
| 6 | 0.071 |
| 7 | 0.061 |
| 8 | 0.057 |
| 9 | 0.010 |
| 10 | 0.009 |
| 11 | 0.017 |
| 12 | 0.008 |
| 13 | 0.006 |
| 14 | 0.007 |
| WO2007/084786 Example 17 | 0.094 |
| WO2007/084786 Example 18 | 0.091 |
| WO2007/084786 Example 85 | 0.016 |
| WO2007/084786 Example 324 | 0.327 |
| WO2007/084786 Example 343 | 0.015 |

| Biochemical PI3Kbeta | |
|---|---|
| Example no. | PI3Kb/IC50 [umol I-1] |
| 1 | 0.009 |
| 2 | 0.096 |
| 3 | 0.007 |
| 4 | 0.159 |
| 5 | 0.031 |
| 6 | 0.460 |
| 7 | 0.110 |
| 8 | 0.067 |
| 9 | 0.015 |
| 10 | 0.005 |
| 11 | 0.010 |
| 12 | 0.007 |
| 13 | 0.011 |
| 14 | 0.006 |
| WO2007/084786 Example 17 | 0.237 |
| WO2007/084786 Example 18 | 0.236 |
| WO2007/084786 Example 85 | 0.015 |
| WO2007/084786 Example 324 | 1.067 |
| WO2007/084786 Example 343 | 0.027 |

| Biochemical PI3Kdelta | |
|---|---|
| Example no. | PI3Kd/IC50 [umol I-1] |
| 1 | 0.003 |
| 2 | 0.027 |
| 3 | 0.004 |
| 4 | 0.066 |
| 5 | 0.147 |
| 6 | 0.079 |
| 7 | 0.041 |
| 8 | 0.026 |
| 9 | 0.010 |
| 10 | 0.031 |
| 11 | 0.014 |
| 12 | 0.004 |
| 13 | 0.003 |
| 14 | 0.016 |
| WO2007/084786 Example 17 | 0.848 |
| WO2007/084786 Example 18 | 1.978 |
| WO2007/084786 Example 85 | 0.024 |
| WO2007/084786 Example 324 | 1.219 |
| WO2007/084786 Example 343 | 0.110 |

| Biochemical PI3Kgamma | |
|---|---|
| Example no. | PI3Kg/IC50 [umol I-1] |
| 1 | 0.092 |
| 2 | 5.8 |
| 3 | 0.110 |
| 4 | 4.5 |
| 5 | 3.5 |
| 6 | 7 |
| 7 | 3 |
| 8 | 0.580 |
| 9 | 0.230 |
| 10 | 0.343 |
| 11 | 0.102 |
| 12 | 0.135 |
| 13 | 0.100 |
| 14 | 0.027 |
| WO2007/084786 Example 17 | 3.36 |
| WO2007/084786 Example 18 | 7.35 |
| WO2007/084786 Example 85 | 0.315 |
| WO2007/084786 Example 324 | 4.46 |
| WO2007/084786 Example 343 | 0.170 |

| Binding assay mTor | |
|---|---|
| Example no. | mTor/IC50 [umol l-1] |
| 1 | 0.251 |
| 2 | 2.8 |
| 3 | 0.850 |
| 4 | >9.7 |
| 5 | 2.25 |
| 6 | 4.7 |
| 7 | 2.7 |
| 8 | 0.960 |
| 9 | |
| 10 | 1.01 |
| 11 | 0.870 |
| 12 | 0.750 |
| 13 | 0.230 |
| 14 | 0.490 |
| WO2007/084786 Example 17 | 5.06 |
| WO2007/084786 Example 18 | 3.3 |
| WO2007/084786 Example 85 | 2.35 |
| WO2007/084786 Example 324 | >9.55 |
| WO2007/084786 Example 343 | >10 |

| Cellular assay PI3Kalpha | |
|---|---|
| Example no. | Rat1-PI3Ka/IC50 [umol l-1] |
| 1 | 0.031 |
| 2 | 1.07 |
| 3 | 0.074 |
| 4 | 0.597 |
| 5 | 0.434 |
| 6 | 0.930 |
| 7 | 0.452 |
| 8 | 0.173 |
| 9 | 0.029 |
| 10 | 0.085 |
| 11 | 0.032 |
| 12 | 0.063 |
| 13 | 0.126 |
| 14 | 0.046 |
| WO2007/084786 Example 17 | 0.369 |
| WO2007/084786 Example 18 | 0.606 |
| WO2007/084786 Example 85 | 0.127 |
| WO2007/084786 Example 324 | 1.730 |
| WO2007/084786 Example 343 | >10 |

| Cellular assay PI3Kbeta | |
|---|---|
| Example no. | Rat1-PI3Kb/IC50 [umol l-1] |
| 1 | 0.020 |
| 2 | 0.751 |
| 3 | 0.033 |
| 4 | 0.757 |
| 5 | 0.201 |
| 6 | 0.420 |
| 7 | 0.430 |
| 8 | 0.026 |
| 9 | 0.254 |
| 10 | 0.023 |
| 11 | 0.026 |
| 12 | 0.064 |
| 13 | <0.003 |
| 14 | 0.007 |
| WO2007/084786 Example 17 | 1.54 |
| WO2007/084786 Example 18 | 1.58 |
| WO2007/084786 Example 85 | 0.156 |
| WO2007/084786 Example 324 | 5.31 |
| WO2007/084786 Example 343 | >10 |

| Cellular assay PI3Kdelta | |
|---|---|
| Example no. | Rat1-PI3Kd/IC50 [umol l-1] |
| 1 | 0.0113 |
| 2 | 0.105 |
| 3 | 0.006 |
| 4 | 0.298 |
| 5 | 0.119 |
| 6 | 0.144 |
| 7 | 0.123 |
| 8 | 0.028 |
| 9 | 0.011 |
| 10 | 0.022 |
| 11 | 0.020 |
| 12 | 0.004 |
| 13 | <0.003 |
| 14 | 0.004 |
| WO2007/084786 Example 17 | 1.04 |
| WO2007/084786 Example 18 | 1.47 |
| WO2007/084786 Example 85 | 0.139 |
| WO2007/084786 Example 324 | 6.54 |
| WO2007/084786 Example 343 | 0.105 |

| Cellular assay mTOR | |
|---|---|
| Example no. | mTOR S6K(T389)_TSC1ko/ IC50 [umol l-1] |
| 1 | 0.243 |
| 2 | >2.27 |
| 3 | 0.159 |
| 4 | >2.27 |
| 5 | 0.371 |
| 6 | >2.27 |
| 7 | >2.27 |
| 8 | >4.55 |
| 9 | |
| 10 | 0.221 |
| 11 | 0.747 |
| 12 | 0.274 |
| 13 | 1.07 |
| 14 | 0.724 |
| WO2007/084786 Example 17 | 2.12 |

-continued

Cellular assay mTOR

| Example no. | mTOR S6K(T389)_TSC1ko/ IC50 [umol I-1] |
|---|---|
| WO2007/084786 Example 18 | >2.27 |
| WO2007/084786 Example 85 | 1.03 |
| WO2007/084786 Example 324 | >2.27 |
| WO2007/084786 Example 343 | >2.27 |

Photostability

Samples investigated for light stability were treated in a light stability chamber (Atlas CPS+, Serial Number 0704013). Solutions of 1.0 mg/nnl in ethanol were prepared for each molecule and aliquots of 0.5 mL were dispensed into suitable micro tubes. All measurements were done in duplicate and compared to a reference wrapped in aluminium foil during light exposure. Solutions were exposed to 19620 kJ/m$^2$ over 13 h. Samples were kept at 15° C. during the experiment. After treatment in the light chamber, the solutions were analyzed by UPLC (UPLC 1, experimental part) at 254 nm. The peak areas were automatically integrated, and the degradation percentage calculated as the difference between the corresponding peak area percentage of the reference sample and the average peak area percentage of the exposed samples (duplicate).

The data obtained using this method is shown in the following table:

| Example no. | % degradation in photostability assay (average) |
|---|---|
| 1 | 8% |
| 2 | 3% |
| 3 | 3% |
| 5 | 17% |
| 6 | 0% |
| 10 | 7% |
| 12 | 12% |
| 13 | 4% |
| 14 | 8% |
| WO2007/084786 Example 17 | 82% |
| WO2007/084786 Example 18 | 81% |
| WO2007/084786 Example 85 | 40% |
| WO2007/084786 Example 324 | 54% |
| WO2007/084786 Example 343 | 31% |

Anti-proliferative Inhibition on the Proliferation of Cell Lines
Cells and Cell Cultures Used for Compound Profiling The SCL-1 and SCC12B2 are human cutaneous squamous cell carcinoma (SCC) cell lines derived from naturally occurring, poorly differentiated SCCs. The SCL-1 cell line was originally established in the lab of N. Fusenig at the Cancer Research Center in Heidelberg, and its growth characteristics in vitro in comparison with normal keratinocytes were described previously (Neely et al 1991). The SCC12B2 cell line was established as described previously (Rheinwald & Beckett 1981) from the facial skin of a male transplant patient who received immunosuppressive therapy for 7 years. The human SCC cell line Detroit562 was obtained from American Tissue Culture Collection (ATCC). Detroit562 is referred to as Head&Neck squamous cell carcinomas (HNSCC) and was derived from a pharyngeal SCC tumor. The Detroit562 cell line bears the activating mutation H1047R of the PIK3CA gene. This mutation is known as one of the "hotspot" mutations of p110α-chain rendering this kinase isoform constitutively active and stimulating the Akt/mTOR pathway independent of growth factor receptor activation. All SCC cell lines were maintained and cultured in Dulbecco modified Eagle's medium (DMEM) medium (Gibco; catalog number: #10938) which was further supplemented with 5% FCS (Gibco; #16000-044), 100 μM sodium-pyruvat (Gibco; #11360-039), 10 mM HEPES (Gibco; #91002-066), 50 U/ml penicillin and 50 μg/ml streptomycin mixture (Gibco; #15070-063), and 2 mM L-glutamine (Gibco; #25030-024). All concentrations are given as final concentrations. Cell were propagated in Corning Costar flasks with ventilation caps, using either of two flask sizes with 75 cm2 (Corning; #430641), or 150 cm2 (Corning, #430825) growth areas. The cell cultures were routinely maintained at 37° C. in an atmosphere containing 5% CO2 and 80% relative humidity (Heraeus type).

Measurement of Cell Proliferation

Cells of SCC or keratinocyte lines (Detroit562, SCC12B2, SCL1, HaCaT) were used for the proliferation assays when they had reached about 80% to 90% confluency. Cells were then harvested after trypsin-mediated dislodgement from culture flasks, washed in culture medium containing 10% FCS, counted in a hemocytometer and diluted complete culture medium with 5% FCS to obtain a cell density of 5×10$^4$ cells/ml. 100 μl of this cell suspension (e.g. 5000 cells) were transferred into each well of a 96-well white walled tissue culture plate (Corning-Costar article #3917). Cells were then allowed to settle by placing them in the CO$_2$ incubator for 45 to 60 minutes. Subsequently, a volume of 100 μl of culture medium containing twice the desired final concentration of the test compound was added to each well of quadruplicate wells. One quadruplicate received 100 μl culture medium without test article as control (indicated in the data figures with the abbreviation no cpd on the x-axis). The cell cultures were then incubated in the presence or absence of the test compounds for a total of 26 to 28 hours. The cell proliferation was determined on the basis of incorporation of bromodesoxy-uridin (BrdU) into cellular DNA using the chemiluminescent BrdU Cell Proliferation ELISA (Roche article #11 669 915 001). Briefly, the BrdU reagent was diluted 1:100 with complete culture medium to obtain a concentration of 100 μM BrdU. From this solution, 20 μl were added to each well and the cell culture was further incubated for 16 to 18 hours at 37° C. at 5% CO$_2$. The proliferation assay was stopped after 44 to 46 hours by complete removal of the culture medium and addition of 200 μl fixing solution (provided with the ELISA kit) for 30 minutes at room temperature. All further incubations, washings and assay development procedures were performed exactly as described in the ELISA assay manual provided by the manufacturer (Roche). Incorporation of BrdU into the DNA was detected by BrdU-specific antibodies and quantified on the basis of an antibody-coupled luciferase mediated signal generation. The luminescence emission was measured in a Victor light 1420 Luminescence counter, (Perkin Elmer) and expressed as relative luminescence units (e.g. data points given as RLU/s) per second. The data points of each well were transferred to the Windows® Excel spreadsheets for calculation of mean and standard deviation values. These values were plotted using the sigmoidal curve fitting function available in the Origin 7.5® software.

Anti-proliferative Potency of Compounds Measured in SCC Cell Lines

The data obtained using these SCC and keratinocyte cell lines are shown in the following table. All values indicating the anti-proliferative potency represent the nanomolar $IC_{50}$ concentrations obtained in two independent assays using either SCC cell lines SCL-1, SCC12B2, Detroit562 or the HaCaT keratinocyte cell line:

| Example no. | SCC12B2 | | SCL-1 | | Detroit562 | | HaCaT | |
|---|---|---|---|---|---|---|---|---|
| measurement | #1 | #2 | #1 | #2 | #1 | #2 | #1 | #2 |
| Example 1 | 1289 | 703 | 351 | 268 | 598 | 440 | 282 | 298 |
| WO2007/084786 Example 17 | 5823 | 4938 | 4891 | 3302 | 3084 | 4408 | 2796 | 3961 |
| WO2007/084786 Example 18 | 5737 | 5250 | 4267 | 3267 | 2813 | 4550 | 1655 | 3078 |
| WO2007/084786 Example 85 | 1645 | 1144 | 1025 | 636 | 1905 | 1448 | 1057 | 1017 |
| WO2007/084786 Example 324 | 6296 | | 6040 | | 3304 | | 3700 | |
| WO2007/084786 Example 343 | 4861 | 2471 | 2624 | 1683 | 2393 | 1371 | 1616 | 1490 |

All values are nanomolar $IC_{50}$ concentrations

Skin Penetration

The skin penetration/permeation properties of one representative compound of the present invention were tested as follows:

In vitro Test to Determine Skin Penetration and Permeation Properties

The compound was applied as 0.5% solutions in propylene glycol mixed with either ethanol or oleylalcohol to pig skin mounted in static Franz-type diffusion cells. At the end of a 48 hours exposure time, drug concentrations were measured in the skin (after removal of stratum corneum) and in the receiver. The receiver solution is a mixture of two volume parts of phosphate-buffered saline (PBS) and one volume part of fetal calf serum (FCS).

| | | | | Skin penetration and permeation in vitro | |
|---|---|---|---|---|---|
| Example | Skin source [a] | Formulation | Concentration [%] of compound | Skin concentration [µg/g] | Permeation rate [ng/cm²/hr] |
| 1 | Pig | PG + ethanol (7 + 3) [b] | 0.5 | 10.8 ± 1.7 | 1.0 ± 0.3 |
| 1 | Pig | PG/OA (9 + 1) [c] | 0.5 | 107.6 ± 31.4 | 301.1 ± 129.5 |

Skin concentrations are given as mean ± standard deviation of quadruplicate determinations.
[a] skin was derived from 4 months old farm pigs (Landrace x Deutsches Edelschwein)
[b] 7 volume parts of propylene glycol (PG) mixed with of 3 volume parts of ethanol
[c] 9 volume parts of PG mixed with 1 volume part of oleylalcohol (OA)

The compound of example 1 penetrates well into pig skin in vitro, while permeation rate through pig skin is low, indicating a low systemic exposure. Pig skin is similar to human skin regarding barrier function and architecture.

In vivo Test to Determine Penetration into Dermis of Topically Treated Pigs

Small skin areas (4 cm²) on the dorsolateral back of young domestic pigs were treated topically with 0.5% solutions or suspensions at different time intervals (2 and 24 h) prior to drug level determination. In this experiment, 4 pigs were treated, and the compound administered in the respective formulation at 4 different sites. Skin flaps with the treated sites in the centre were dissected and removed. The skin flaps were spread, and heated metal blocks placed on the test sites for 1 minute to induce separation of epidermis from the dermis. After removal of the loosened epidermal sheets, 1 mm thick dermal sheets were prepared from the treated, de-epidermized skin with a dermatome. From these sheets 6 mm punch samples (6 mm Ø) were collected and analysed for test compound concentration by LC/MS. The procedure described was done with careful avoidance of contamination of the dermal samples with compound attached superficially to the epidermis.

The following table provides dermal concentrations of the compound of example 1 in pig dermis when applied epicutaneously in the identified formulations. The data table provides the mean±standard error of the mean of 8 determinations (e.g. eight skin samples analyzed for each time point).

| | | Skin PK in vivo in pigs | |
|---|---|---|---|
| Example | Composition of formulation with compound added to 0.5% | Dermis concentration [µg/g] measured after 2 h | Dermis concentration [µg/g] measured after 24 h |
| 1 | 1% Tween ®80, 98% water, 1% HPMC | 0.95 ± 0.42 | 1.29 ± 0.54 |
| 1 | 10% OA, 89% water, 1% Sepineo | 2.58 ± 0.48 | 0.37 ± 0.13 |
| 1 | 10% EtOH, 89% water, 1% HPMC | 1.57 ± 0.52 | 0.66 ± 0.38 |
| 1 | 10% EtOH, 10% PG, 79% water, 1% HPMC | 0.68 ± 0.2 | 0.52 ± 0.24 |

Mean ± standard error mean of eight determinations are given.
Tween ®80: polyoxyethylenesorbitan monooleate
OA: oleylalcohol
PG: propylene glycol
EtOH: ethanol
HPMC: hydroxypropylmethylcellulose The compound of example 1 penetrates well into pig skin reaching the dermis in vivo after a single application.

What is claimed is:

1. A compound and/or a pharmaceutically acceptable salt and/or solvate thereof, of the formula,

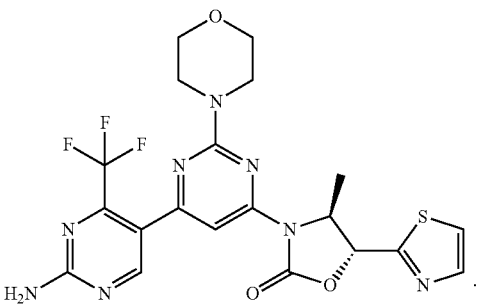 [SMILES: C[C@H]1[C@H](c2nccs2)OC(=O)N1c1cc(-c2cnc(N)nc2C(F)(F)F)nc(N2CCOCC2)n1 ; "."]

2. A pharmaceutical composition comprising a therapeutically effective amount of a compound according to claim 1, or a pharmaceutically acceptable salt thereof, and one or more pharmaceutically acceptable carriers.

3. A combination comprising a therapeutically effective amount of a compound according to claim 1, or a pharmaceutically acceptable salt thereof, and one or more therapeutically active co-agents.

4. A method of treating non-melanoma skin cancers, pre-malignant stages of non-melanoma skin cancers or hyperproliferative skin disorders caused by dysregulation of skin fibroblasts in a subject comprising administering to the subject a therapeutically effective amount of the compound, or a pharmaceutically acceptable salt thereof, according to claim 1.

5. A method of treating keloids in a subject comprising administering to the subject a therapeutically effective amount of the compound, or a pharmaceutically acceptable salt thereof, according to claim 1.

* * * * *